(12) United States Patent
Xi et al.

(10) Patent No.: US 11,008,361 B2
(45) Date of Patent: May 18, 2021

(54) LIVER-SPECIFIC DELIVERY-BASED ANTI-HEPATITIS C PRODRUG NUCLEOSIDE CYCLO-PHOSPHATE COMPOUND AND USES THEREOF

(71) Applicant: ZHEJIANG PALO ALTO PHARMACEUTICALS,INC, Zhejiang (CN)

(72) Inventors: Zhijian Xi, Zhejiang (CN); Huaqiang Xu, Zhejiang (CN); Chunping Lu, Zhejiang (CN); Zhongshan Wu, Zhejiang (CN); Feng Sun, Zhejiang (CN)

(73) Assignee: ZHEJIANG PALO ALTO PHARMACEUTICALS, INC., Quzhou (CN)

( * ) Notice: Subject to any disclaimer, the term of this patent is extended or adjusted under 35 U.S.C. 154(b) by 0 days.

(21) Appl. No.: 16/656,595

(22) Filed: Oct. 18, 2019

(65) Prior Publication Data
US 2020/0048299 A1 Feb. 13, 2020

Related U.S. Application Data

(63) Continuation of application No. PCT/CN2018/083420, filed on Apr. 17, 2018.

(30) Foreign Application Priority Data

Apr. 18, 2017 (CN) .......................... 201710254376.9

(51) Int. Cl.
| A61K 31/7072 | (2006.01) |
| A61P 31/14 | (2006.01) |
| C07H 19/11 | (2006.01) |
| A61K 45/06 | (2006.01) |

(52) U.S. Cl.
CPC .............. *C07H 19/11* (2013.01); *A61P 31/14* (2018.01); *A61K 45/06* (2013.01)

(58) Field of Classification Search
CPC ...... A61K 31/7072; A61P 31/14; C07H 19/11
See application file for complete search history.

(56) References Cited

FOREIGN PATENT DOCUMENTS

| CN | 103848877 A | 6/2014 |
| CN | 106164939 A | 11/2016 |
| WO | 2009073506 A2 | 6/2009 |

OTHER PUBLICATIONS

Brett C Bookser et al. "High-Throughput Synthesis of HepDirect Prodrugs of Nucleoside Monophosphates", Journal of Combinatorial Chemistry, May 29, 2018; ISSN:1520-4766.

*Primary Examiner* — Brenda L Coleman

(57) ABSTRACT

Disclosed herein are a liver specific delivery (LSD)-based antiviral prodrug nucleoside cyclophosphate compound and uses thereof. Specifically, this application provides a compound of formula (I), or an isomer, a pharmaceutically acceptable salt, a hydrate, a solvate or a pharmaceutical composition thereof. This application also provides an application of the compound alone or in combination with other antiviral drugs in the treatment for viruses, particularly hepatitis C virus (HCV).

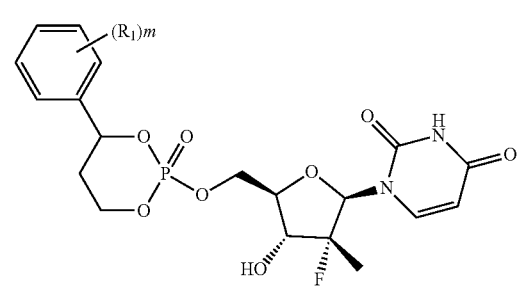

9 Claims, 4 Drawing Sheets

LIVER-SPECIFIC DELIVERY-BASED ANTI-HEPATITIS C PRODRUG NUCLEOSIDE CYCLO-PHOSPHATE COMPOUND AND USES THEREOF

CROSS-REFERENCE TO RELATED APPLICATIONS

This application is a continuation of International Patent Application PCT/CN2018/083420, filed on Apr. 17, 2018, which claims the benefit of priority from Chinese Patent Application No. 201710254376.9, filed on Apr. 18, 2017. The content of the aforementioned application, including any intervening amendments thereto, is incorporated herein by reference.

TECHNICAL FIELD

The present invention relates to a preparation method and an application of a liver-specific delivery-based antiviral prodrug nucleoside cyclo-phosphate compound or an optical isomer, a hydrate, a solvate, a pharmaceutically acceptable salt or a pharmaceutical composition thereof.

BACKGROUND OF THE INVENTION

Hepatitis C virus (HCV) is a main human pathogen and there are about 200 million cases infected with HCV worldwide. Chronic HCV infection will develop into serious progressive liver diseases, including cirrhosis and hepatocellular carcinoma. Therefore, chronic HCV infection is the major cause of death worldwide in patients who suffer from liver diseases. According to the data released by the Health Planning Commission, the reported cases of hepatitis C virus infection in China has continuously increased in the past 10 years, and the general trend is still not optimistic.

HCV is a positive-strand RNA virus, and its genome consists of approximately 9,600 nucleotides, including non-coding regions at both ends, i.e., an internal ribosome entry site (IRES) and an open reading frame (ORF). HCV genome includes 10 genes that respectively express 10 structural proteins (a core protein, envelope proteins E1 and E2, an ion channel protein P7) and non-structural proteins (NS2, NS3, NS4A, NS4B, NS5A and NS5B), where NS5B has a RNA-dependent RNA polymerase activity and is involved in the replication of HCV genome.

The precursor structure of a cyclo-phosphate (e.g., 4-aryl-2-oxo-1,3,2-dioxaphosphane) has good liver delivery and the mechanism of the liver delivery is very clear. As shown in FIG. 1, the 4-aryl substitution position is specifically catalyzed to form a hydroxyl group by CYP3A which belongs to a cytochrome P450 isozyme family in hepatocytes, and then the resulting product undergoes a ring-opening reaction to form a negatively-charged phosphate intermediate which has difficulty in passing through the cell membrane to exist in the cell. Then the phosphate intermediate is subjected to hydrolysis and β-elimination reaction in the presence of phosphodiesterase to form a nucleoside monophosphate compound (2-FM UMP), which is further catalyzed with a nucleotide kinase to produce a biologically-active nucleoside triphosphate compound (2-FM UTP). At the same time, the metabolic by-product aryl vinyl ketone can be removed by 1,4-addition reaction with glutathione which has antioxidant and anti-free radical activities and is abundant in liver cells. In addition, it has not been reported with respect to the side effects of the resulting additive product. The nucleoside monophosphate compound (2-FM UMP) can also be dephosphorylated to give a corresponding nucleoside (2-FM UR).

Patent application WO2009073506 A2 uses sofosbuvir (SFB) as an active ingredient which reacts with a cyclic phosphate ester and an aromatic ring substituent for prodrug structural modification, and then the modified product undergoes propyl esterification at the 3-position hydroxyl group to produce 87.8 nmol/g of the corresponding active triphosphate compound in rat hepatocytes with lamivudine triphosphate used as a reference.

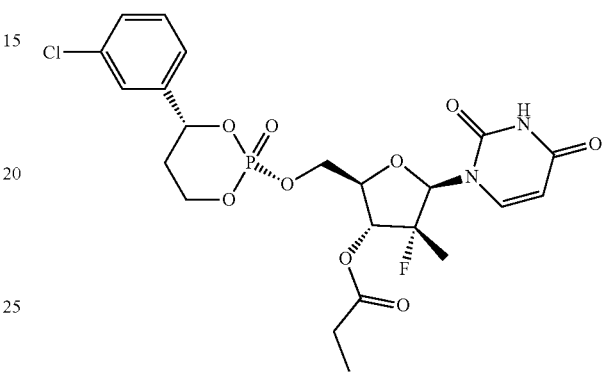

Among the commercially available anti-hepatitis C drugs, sofosbuvir is the only one targeting NS5B. But the FDA has warned in March 2015 that serious brdycardia may occur in the case that sofosbuvir is used to treat the HCV in combination with other antiviral drugs and amiodarone. In addition, sofosbuvir is not suitable for the patients suffering from severe renal impairment (eGFR<30 mL/min/1.73 m2).

There is currently a lack of virus-inhibiting compounds with high activity, good liver delivery and low toxic side effects. Therefore, there is an urgent need in the art to develop a novel virus-inhibiting compound having high activity, good liver delivery and low toxic side effects.

SUMMARY

An antiviral nucleoside cyclo-phosphate compound is synthesized herein, and modified with respect to the aromatic ring substituent to give a class of liver specific delivery-based prodrugs, which have better efficacy and lower toxic side effects.

In a first aspect, the invention provides a compound of formula (I) or an optical isomer, a pharmaceutically acceptable salt, a hydrate or a solvate thereof:

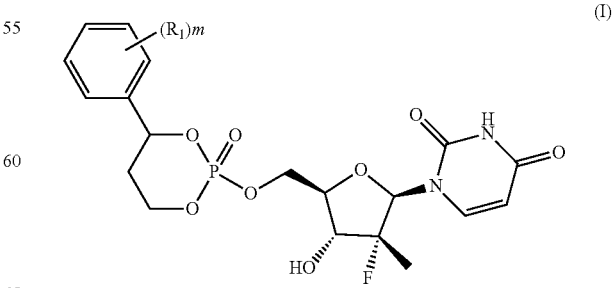

wherein each $R_1$ independently selected from halogen, nitro, hydroxyl, amino, cyano group, substituted or unsubstituted $C_1$-$C_6$ alkyl, substituted or unsubstituted $C_3$-$C_8$ cycloalkyl, substituted or unsubstituted $C_1$-$C_6$ alkoxy, substituted or unsubstituted $C_1$-$C_6$ alkylamino, substituted or unsubstituted $C_1$-$C_6$ carboxyl, unsubstituted or unsubstituted $C_1$-$C_6$ ester group, substituted or unsubstituted $C_2$-$C_6$ alkanoyl or substituted or unsubstituted $C_2$-$C_6$ alkylamido; where the substituted groups comprise one or more substituents selected from halogen, $C_1$-$C_3$ alkyl, $C_1$-$C_3$ haloalkyl, nitro, hydroxyl, amino and cyano group;

m is 0, 1, 2, 3, 4 or 5.

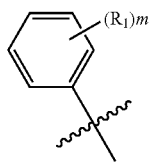

In an embodiment, is selected from:

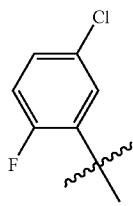 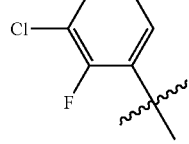 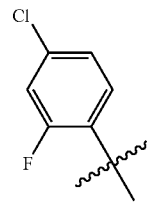

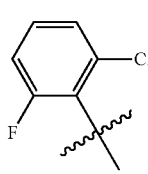 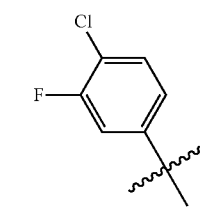 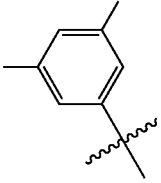

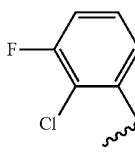 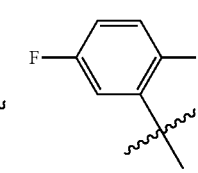 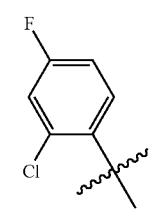

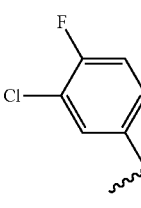 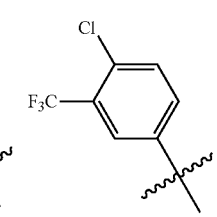 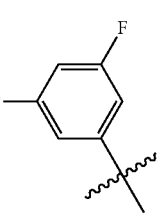

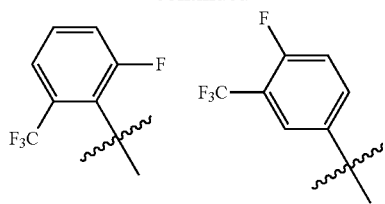

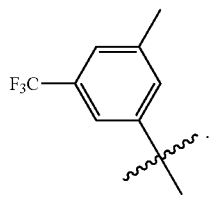

In an embodiment, the compound of formula (I) has a structure selected from:

(II)

(III)

wherein n is 0, 1, 2 or 3;

$R_2$ and $R_3$ are independently selected from fluorine, chlorine, bromine or iodine;

and each chiral center is R-configuration or S-configuration in formula (II) and formula (III).

In an embodiment, $R_2$ is chlorine and $R_3$ is fluorine; or $R_2$ is fluorine and $R_3$ is chlorine.

In an embodiment, the optical isomer comprises tautomer, cis-trans isomerism, configurational isomer, meso compound, and optical isomer having enantiomeric or diastereomeric relationships.

In an embodiment, the compound is selected from:

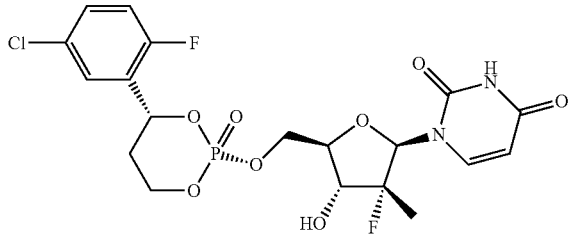

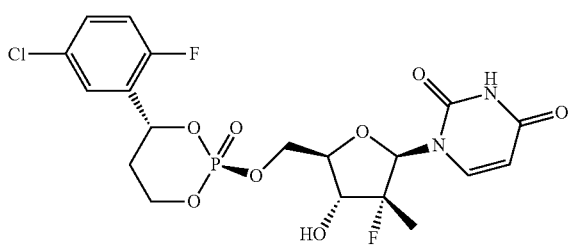

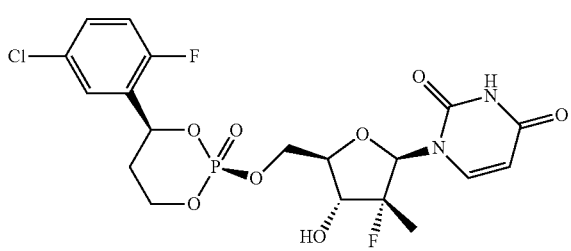

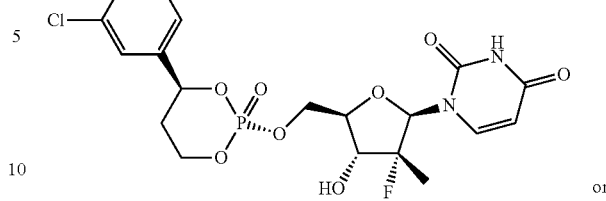

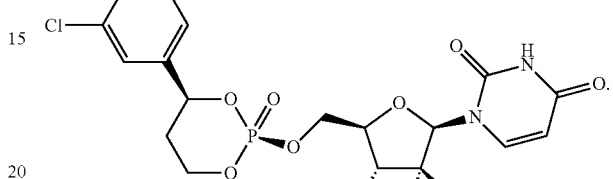

In an embodiment, the salts of the compounds as shown in formula (I), formula (II) and formula (III) are pharmaceutically acceptable salts formed by reactions of the compounds of formula (I), formula (II) and formula (III) with inorganic or organic acids. Or salts of the compounds of the formula (I), formula (II) and formula (III) are pharmaceutically acceptable salts formed by reactions of the compounds of the formula (I), formula (II) and formula (III) with bases. The compound of the formula (I), the formula (II) and the formula (III) or the salt thereof is an amorphous substance or a crystal.

In a second aspect, the invention provides a pharmaceutical composition comprising a therapeutically effective amount of the compound or an optical isomer, a pharmaceutically acceptable salt, a hydrate or a solvate thereof according to the first aspect, and a pharmaceutically acceptable auxiliary, diluent or carrier.

In a third aspect, the invention provides use of the compound or an optical isomer, a pharmaceutically acceptable salt, a hydrate or a solvate thereof in the manufacture of a pharmaceutical composition for treating and/or preventing an acute or chronic disease associated with hepatitis C virus (HCV) infection.

In a forth aspect, the invention provides a method for preparing a compound of formula (II) described in the first aspect of the invention, which comprises the following step:

(i-a) removing TBS from a compound of formula (IIa) in an inert solvent in the presence of a TBS-removal reagent to form a compound of formula (II)

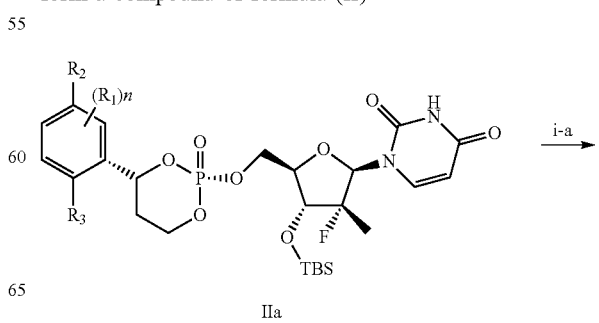

-continued

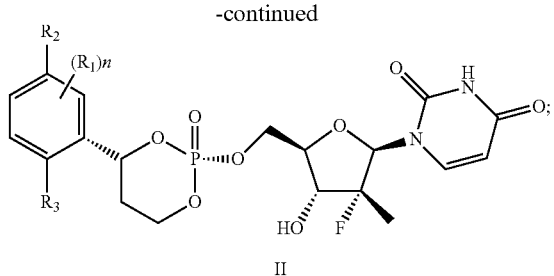

in the formula, each group is defined as above.

In an embodiment, the TBS-removal reagent in the step (i-a) is selected from tetrabutylammonium fluoride (TBAF), glacial acetic acid, dilute hydrochloric acid or a combination thereof, preferably tetrabutylammonium fluoride (TBAF).

In an embodiment, the inert solvent in the step (i-a) is selected from N, N-dimethylformamide, tetrahydrofuran or a combination thereof, preferably tetrahydrofuran.

In an embodiment, the reaction temperature of the step (i-a) is −50-30° C., preferably about 25±5° C.

In an embodiment, a time of the deprotection reaction in step (i-a) is 0.5-6 h, preferably 0.5-3 h, and more preferably 0.5-2 h.

In a fifth aspect, the invention provides a method for preparing the compound of formula (III), which comprises the following step:

(i-b) removing TBS from a compound of formula (IIIa) in an inert solvent in the presence of a TBS-removal reagent to form a compound of formula (III)

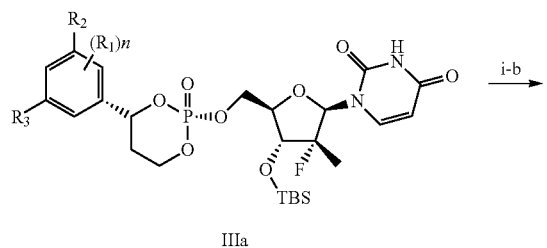

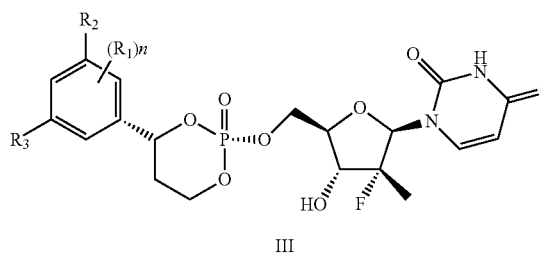

in the formula, each group is defined in the same manner as above.

In an embodiment, the TBS-removal reagent in the step (i-b) is selected from tetrabutylammonium fluoride (TBAF), glacial acetic acid, dilute hydrochloric acid or a combination thereof, preferably tetrabutylammonium fluoride (TBAF).

In an embodiment, the inert solvent in the step (i-b) is selected from N, N-dimethylformamide (DMF), tetrahydrofuran, or a combination thereof, preferably tetrahydrofuran.

In an embodiment, the reaction temperature in the step (i-b) is −50-30° C. preferably about 25±5° C.

In an embodiment, a time of the deprotection reaction in the step (i-b) is 0.5-6 h, preferably 0.5-3 h, more preferably 0.5-2 h.

In an embodiment, the compound of formula (IIa) is prepared by the following step:

(i-c) subjecting a compound of formula (IIb) and a compound of formula (IIc) to substitution reaction in an inert solvent to produce the compound of formula (IIa)

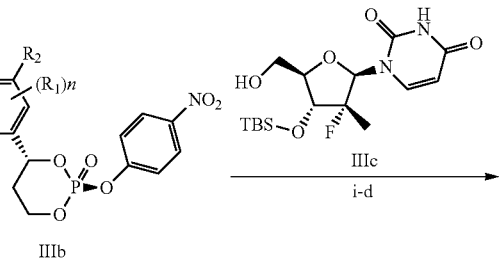

In an embodiment, the reaction is carried out in the presence of a Grignard reagent in the step (i-c), preferably, the Grignard reagent is selected from tert-butylmagnesium chloride (t-BuMgCl).

In an embodiment, the substitution reaction in the step (i-c) is carried out at −50-30° C., preferably at 25±5° C.

In an embodiment, a time of the substitution reaction in the step (i-c) is 1-72 h-, preferably 3-48 h, more preferably 6-24 h In an embodiment, the inert solvent in the step (i-c) is selected from N, N-dimethylformamide, tetrahydrofuran or a combination thereof, preferably tetrahydrofuran In an embodiment, the compound of formula (IIIa) is prepared by the following step:

(i-d) subjecting a compound of formula (IIIb) and a compound of formula (IIIc) to substitution reaction in an inert solvent to produce the compound of formula (IIIa)

-continued

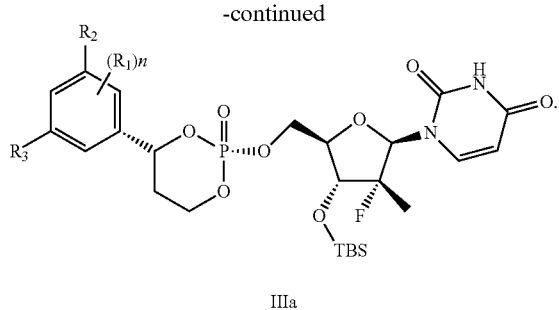

IIIa

In an embodiment, the reaction is carried out in the presence of a Grignard reagent in the step (i-d), preferably, the Grignard reagent is selected from tert-butylmagnesium chloride (t-BuMgCl).

In an embodiment, the substitution reaction of the step (i-d) is carried out at −50-30° C., preferably at 25±5° C.

In an embodiment, a time of the substitution reaction in the step (i-d) is 1-72 h, preferably 3-48 h, more preferably 6-24 h.

In an embodiment, the inert solvent in the step (i-d) is selected from N, N-dimethylformamide (DMF), tetrahydrofuran or a combination thereof, preferably tetrahydrofuran.

It should be understood that various technical features described above and various technical features described hereinafter (for example, in embodiments) of the present invention can be combined with each other to constitute a new or preferred technical solution that will not be described here due to pages of this application.

EXPLANATIONS

Figure 1:
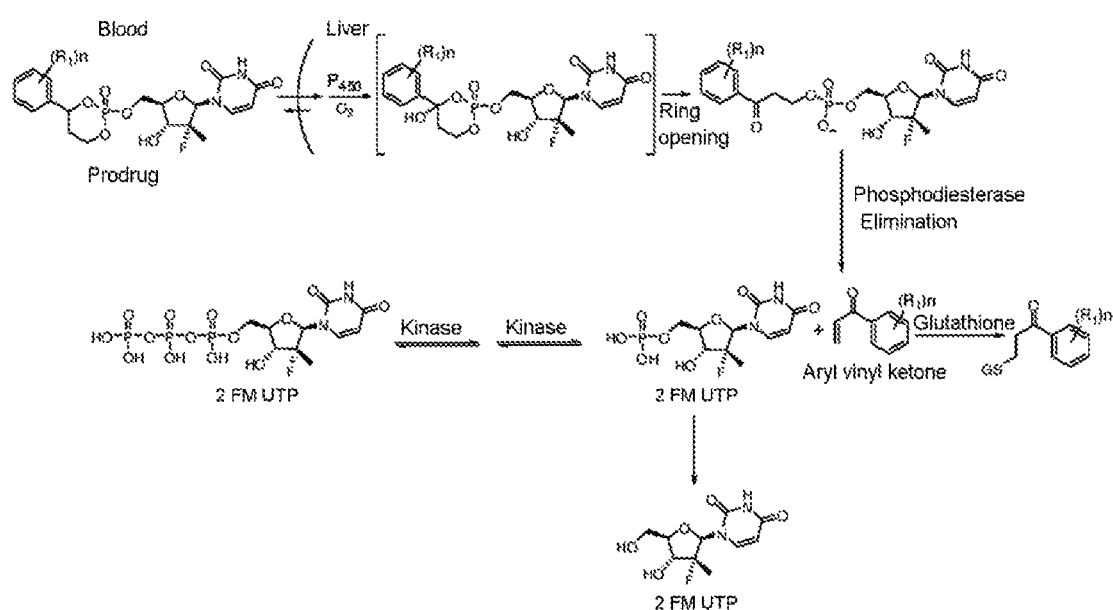
FIG. 1 is a schematic diagram showing the action mechanism of a liver specific delivery-based compound.

2-FM-UR: (2R)-2-deoxy-2-fluoro-2-methyl-uridine;
2-FM-UMP: (2R)-2-deoxy-2-fluoro-2-methyl-uridine-5-monophosphate; and
2-FM-UTP:(2R)-2-deoxy-2-fluoro-2-methyl-uridine-5-triphosphate.

DETAILED DESCRIPTION OF EMBODIMENTS

Through a long-term and in-depth research, the inventor has first found, after the screening and investigation of a large number of compounds, that a class of compounds of formula (II) and formula (III) having specific structures (for example, with different halogens respectively at the 3 and 5 positions on the benzene ring, or different halogens respectively at the 2 and 5 positions on the benzene ring) have excellent antiviral activity, significantly improved liver-specific delivery and significantly reduced toxic side effects. This invention is accomplished based on the above results.

Terminology

As used herein, term "$C_1$-$C_6$ alkyl" refers to a straight or branched alkyl having 1 to 6 carbon atoms, such as methyl, ethyl, propyl, isopropyl, butyl, isobutyl, sec-butyl, a t-butyl, or the like.

As used herein, term "$C_2$-$C_6$ alkanoyl" refers to a substituent "straight or branched alkyl-carbonyl having 2 to 6 carbon atoms", such as acetyl, propionyl, butyryl, or the like.

As used herein, term "$C_1$-$C_6$ alkylamino" refers to a substituent "straight or branched alkyl-amino having 1 to 6 carbon atoms", such as methylamino, dimethylamino, ethylamino, propylamine, diethylamino, or the like.

As used herein, term "halogen" refers to F, Cl, Br or I.

As used herein, term "containing", "including" or "comprising" means that various ingredients may be used together in the mixture or composition of the invention. Therefore, terms "mainly consisting of" and "consisting of" are included in the term "containing".

As used herein, term "pharmaceutically acceptable ingredient" refers to a substance which is suitable for humans and/or animals without excessive adverse effects such as toxicity, irritation and allergy, that is, a substance with a reasonable benefit-risk ratio.

As used herein, term "effective amount" refers to an amount at which a therapeutic agent used can treat, alleviate or prevent a target disease or condition or an amount at which a therapeutic agent used can exhibit a detectable therapeutic or prophylactic effect. A precise effective amount to a subject depends on the size and health of the subject, the nature and extent of the symptom and the selected therapeutic agent and/or combination of therapeutic agents. Therefore, it is useless to specify a precise effective amount in advance. However, for some specific conditions, a clinician is able to determine the effective amount through conventional experiment.

As used herein, term "substitution", unless otherwise specified, means that one or more hydrogen atoms on a group are substituted with a substituent selected from the groups consisting of halogen, $C_1$-$C_3$ alkyl, $C_1$-$C_3$ haloalkyl, nitro, hydroxyl, amino and cyano group.

Unless otherwise specified, all compounds used in the present invention are intended to comprise all possible optical isomers, such as single chiral compounds, or a mixture of various chiral compounds (i.e., racemates). Among all the compounds of the present invention, each of the chiral carbon atoms may be optionally R or S configuration, or a mixture thereof.

As used herein, term "compound of the present invention" refers to a compound of formula (I), formula (II) and formula (III). Such term further involves various crystal forms, pharmaceutically acceptable salts, hydrates or solvates of the compounds of formula (I), formula (II) and formula (III).

As used herein, term "pharmaceutically acceptable salt" refers to a salt formed by the compound of the invention with an acid or base and suitable for use as a medicine. The pharmaceutically acceptable salts include inorganic and organic salts. A preferred class of salts is formed by the compound of the invention with an acid. The acids suitable for forming the salts comprise but are not limited to: inorganic acids such as drochloric acid, hydrobromic acid, hydrofluoric acid, sulfuric acid, nitric acid and phosphoric acid, organic acids such as formic acid, acetic acid, propionic acid, oxalic acid, malonic acid, succinic acid, fumaric acid, maleic acid, lactic acid, malic acid, tartaric acid, citric acid, picric acid, methanesulfonic acid, phenylmethanesulfonic acid and benzenesulfonic acid, and acidic amino acids such as aspartic acid and glutamic acid.

Some of the compounds of the invention may be crystallized or recrystallized with water or various organic solvents, where various solvates may be formed. The solvates of the present invention comprise stoichiometric solvates such as hydrates and compounds containing variable amounts of crystal water formed upon the preparation using lyophilizaton.

It should be understood that various thermodynamically stable isomers may be present after preparation of the compounds of the invention, such as tautomers, conformers, meso compounds, and enantiomers or diastereomers. The above-described variations will be apparent for those skilled in the art after reading the disclosure of the present invention.

Compound (II) and Preparation Thereof

In order to provide a highly efficient, low toxicity liver delivery prodrug of releasing antiviral nucleotides in hepatocytes by a liver delivery mechanism, the inventor have prepared a compound of formula (II):

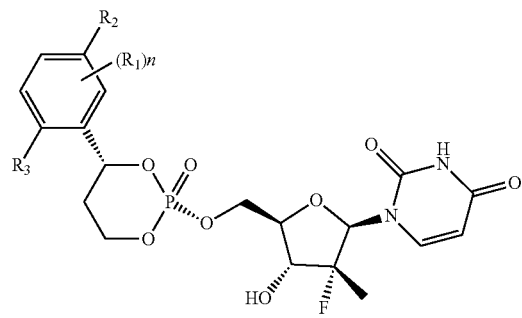

(II)

wherein each $R_1$ is independently selected from halogen, nitro, hydroxyl, amino, cyano group, substituted or unsubstituted $C_1$-$C_6$ alkyl, substituted or unsubstituted $C_3$-$C_8$ cycloalkyl, substituted or unsubstituted $C_1$-$C_6$ alkoxy, substituted or unsubstituted $C_1$-$C_6$ alkylamino, substituted or unsubstituted $C_1$-$C_6$ carboxyl, substituted or unsubstituted $C_1$-$C_6$ ester group, substituted or unsubstituted $C_2$-$C_6$ alkanoyl or substituted or unsubstituted $C_2$-$C_6$ alkylamido; where the substituted groups comprise one or more substituents selected from the group consisting of halogen, $C_1$-$C_3$ alkyl, $C_1$-$C_3$ haloalkyl, nitro, hydroxyl, amino and cyano group;

n is 0, 1, 2 or 3;

$R_2$ and $R_3$ are independently selected from fluorine, chlorine, bromine or iodine;

and each chiral center is R-type or S-type in formula (II).

The compound may be a racemate or an optical isomer, both of which have some antiviral activity. The preferred compound of formula (I) is selected from:

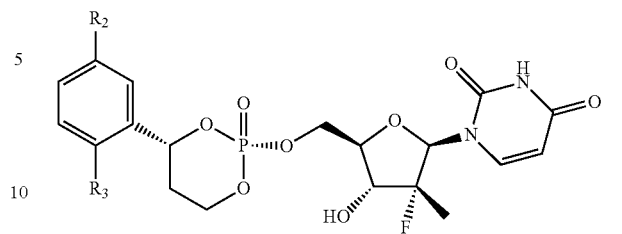

(IIa)

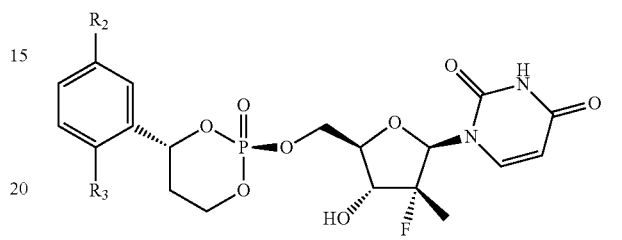

(IIb)

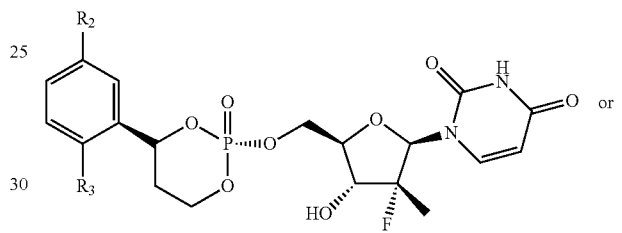

(IIc)

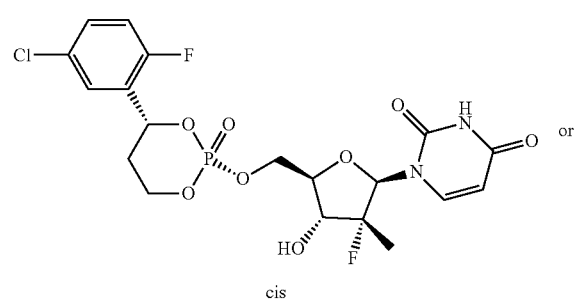

(IId)

In an embodiment, the compound of formula (II) is shown as formula (IIa).

In an embodiment, a relative stereochemistry of P2 and C4 is cis, and P2 is R-configuration, and C4 is S-configuration.

In an embodiment, $R_2$ is chlorine and $R_3$ is fluorine; or $R_2$ is fluorine and $R_3$ is chlorine.

In an embodiment, the optical isomer includes tautomer, cis-trans isomerism, configurational isomer, meso compound, and optical isomer having enantiomeric or diastereomeric relationships.

In an embodiment, the compound is selected from:

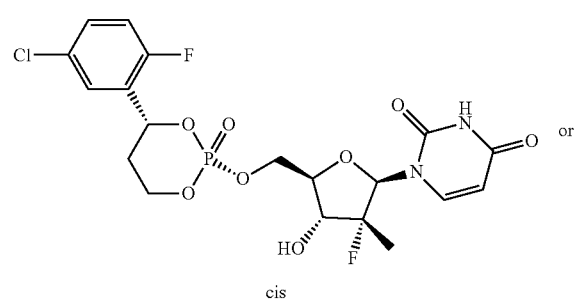

cis

-continued

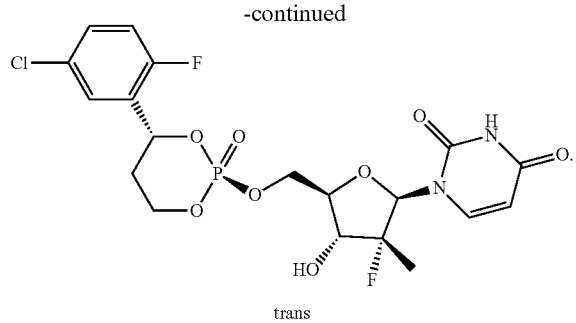

trans

The preparation method of the compound of the general formula (II) is as follows.

A compound of (IIc) is added to a tetrahydrofuran. Tert-butylmagnesium chloride is added dropwise to the solution at 0° C., and the reaction is carried out for 30 min, and then the compound of (IIb) is added one time. The mixture is reacted overnight, quench and purified using silica gel column chromatography to produce an intermediate. The intermediate is dissolved in tetrahydrofuran, to which TBAF is added to remove the protecting group TBS to give the compound of formula (II)

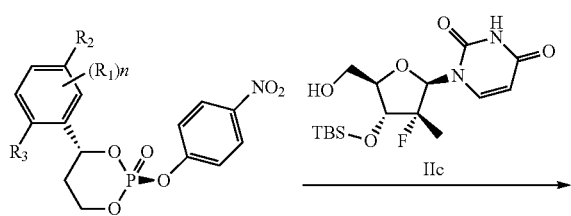

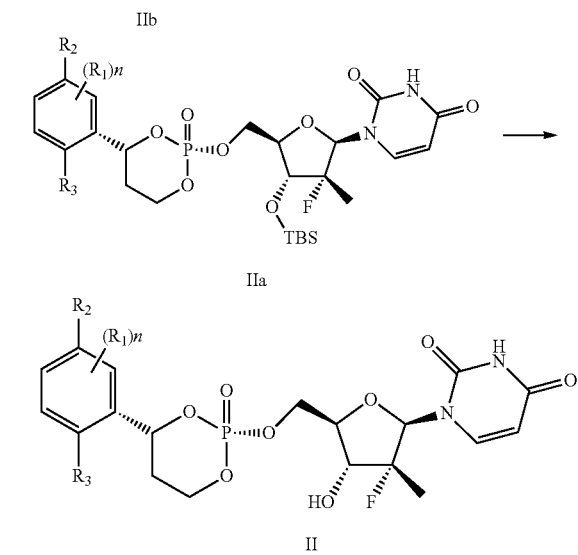

In the above preparation method, each of the reactants may be commercially available or may be prepared by a conventional method in the art using commercially available raw materials.

Compound (III) and Preparation Thereof

A compound of formula (III) is prepared herein to provide a highly efficient, low toxicity liver delivery-based prodrug which is capable of releasing antiviral nucleotides in hepatocytes based on liver-specific delivery:

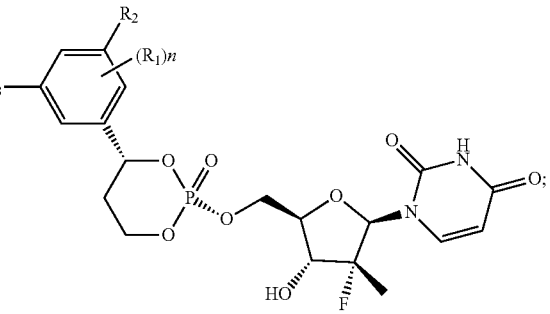

where each $R_1$ is independently selected from halogen, nitro, hydroxyl, amino, cyano group, substituted or unsubstituted $C_1$-$C_6$ alkyl, substituted or unsubstituted $C_3$-$C_8$ cycloalkyl, substituted or unsubstituted $C_1$-$C_6$ alkoxy, substituted or unsubstituted $C_1$-$C_6$ alkylamino, substituted or unsubstituted $C_1$-$C_6$ carboxyl, substituted or unsubstituted $C_1$-$C_6$ ester group, substituted or unsubstituted $C_2$-$C_6$ alkanoyl or substituted or unsubstituted $C_2$-$C_6$ alkylamido; where the substituted groups comprise one or more substituents selected from the group consisting of halogen, $C_1$-$C_3$ alkyl, $C_1$-$C_3$ haloalkyl, nitro, hydroxyl, amino and cyano group;

n is 0, 1, 2 or 3;

$R_2$ and $R_3$ are independently selected from fluorine, chlorine, bromine or iodine; and each chiral center is R-configuration or S-configuration in formula (III).

The compound may be a racemate or an optical isomer, both of which have some antiviral activity. The preferred compound of formula (I) is selected from:

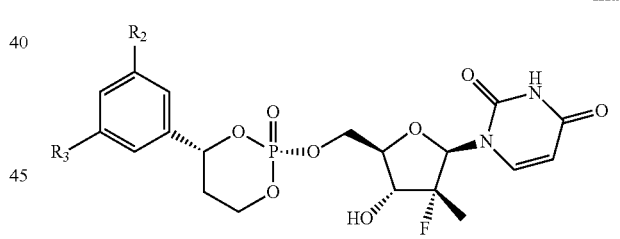

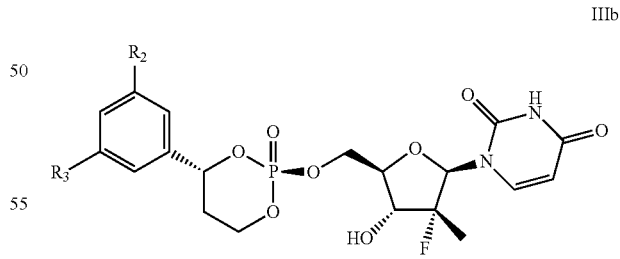

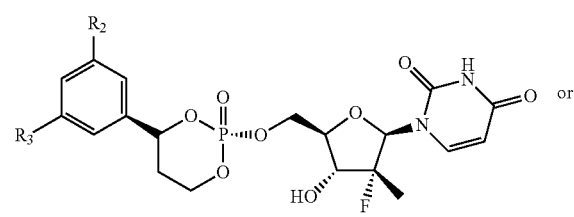

-continued

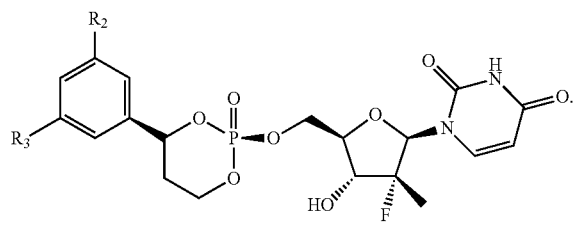

IIId

In an embodiment, the compound of formula (III) is shown as formula (IIIa).

In an embodiment, a relative stereochemistry of P2 and C4 is cis, and P2 is an R-configuration, and C4 is an S-configuration.

In an embodiment, $R_2$ is chlorine and $R_3$ is fluorine; or $R_2$ is fluorine and $R_3$ is chlorine.

In an embodiment, the optical isomer includes tautomer, cis-trans isomerism, configurational isomer, meso compound, and optical isomer having enantiomeric and diastereomeric relationships.

In an embodiment, the compound is selected from:

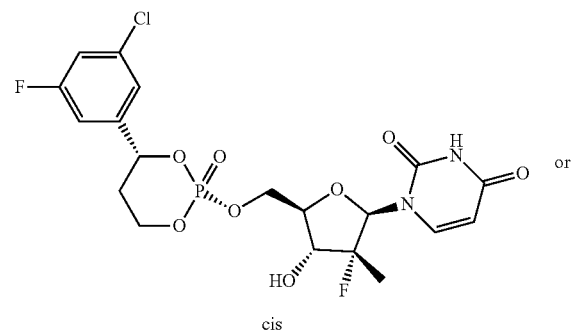

cis trans

The preparation method of the compound of the general formula (III) is as follows.

A compound of formula (IIIc) is added to a tetrahydrofuran. Tert-butylmagnesium chloride is added dropwise to the solution at 0° C., and the reaction is carried out for 30 min, then the compound of formula (IIIb) is added in one batch. The mixture is reacted overnight, quenched and purified using silica gel column chromatography to produce an intermediate. The intermediate is dissolved in tetrahydrofuran, to which TBAF is added to remove the protecting group TBS to give the compound of formula (III)

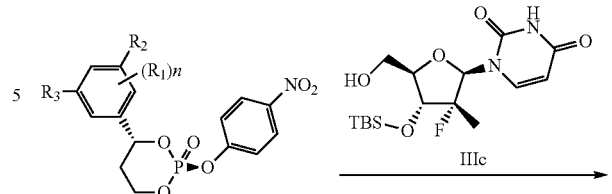

IIIc

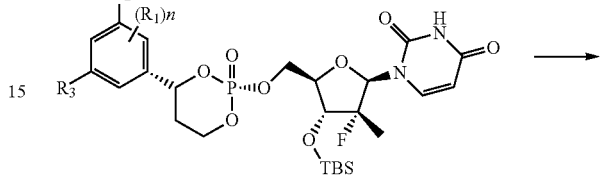

IIIb

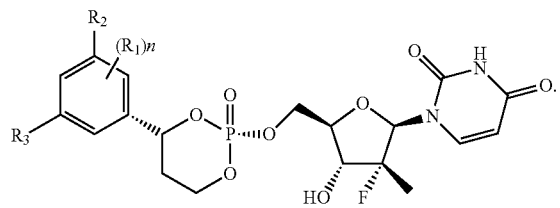

IIIa

III

In the above preparation, each of the reactants may be commercially available or may be prepared by a conventional method in the art using commercially available raw materials.

Pharmaceutical Composition and Administration

Since the compound of the present invention has an excellent inhibitory activity against hepatitis C virus (HCV), the compound of the present invention and various crystal forms, pharmaceutically acceptable inorganic or organic salts, hydrates or solvates thereof, and a pharmaceutical composition containing the compound of the present invention as a main active ingredient all can be used for the treatment, prevention, and alleviation of diseases caused by HCV infection. Based on the prior art, the compound of the invention can be used to treat diseases caused by infections such as HBV, HCV, HIV and HCMV.

The pharmaceutical composition of the present invention comprises the compound of the invention or pharmaceutically acceptable salts thereof at a safe and effective amount and pharmaceutically acceptable excipients or carriers. Where, the "safe and effective amount" refers to an amount at which the compound used is sufficient to significantly improve symptoms without causing serious side effects. Generally, the pharmaceutical composition comprises the compound of the present invention at 0.1-1000 mg per dose, and preferably at 0.5-100 mg per dose. Preferably, the "per dose" refers to a capsule or tablet.

"Pharmaceutically acceptable carrier" refers to one or more solid or liquid fillers or gel materials of compatibility which are suitable for human use and must be of sufficient purity and sufficiently low toxicity. The "compatibility" indicates herein that each component of a composition is capable of blending with each other and with the compound of the invention without significantly reducing the effect of the compound. Parts of the pharmaceutically acceptable carriers comprise cellulose and its derivatives (such as sodium carboxymethylcellulose, sodium ethylcellulose and cellulose acetate), gelatin, talc, solid lubricants (such as stearic acid, magnesium stearate), calcium sulfate, vegetable oils (such as soybean oil, sesame oil, peanut oil and olive oil), polyols (such as propylene glycol, glycerin, mannitol and sorbitol), emulsifiers (such as Tween), wetting agents (such as sodium dodecyl sulfate), colorants, flavoring agents, stabilizers, antioxidants, preservatives and pyrogen-free water.

The administrations of the compound or the pharmaceutical composition of the present invention are not particularly limited, and representative administrations include but are not limited to: oral, rectal, parenteral (intravenous, intramuscular or subcutaneous) and topical administrations, and particularly preferably oral administration.

Solid preparations for oral administration comprise capsule, tablet, pill, powder and granule. In such solid preparations, the active compound is mixed with at least one conventional inert excipient (or carrier), such as sodium citrate or dicalcium phosphate, or mixed with the following components including: (a) a filler or compatibilizer such as starch, lactose, sucrose, glucose, mannitol and silicic acid; (b) a binder such as hydroxymethylcellulose, alginates, gelatin, polyvinylpyrrolidone, sucrose and gum arabic; (c) a humectant such as glycerin; (d) a disintegrating agent such as agar, calcium carbonate, potato starch or tapioca starch, alginic acid, some composite silicates and sodium carbonate; (e) a slow solvent, such as paraffin; (i) an absorbing accelerator, such as quaternary amine compounds; (g) a wetting agent, such as cetanol and glyceryl monostearate; (h) an adsorbent, such as kaoline; and (i) a lubricant, such as talc, calcium stearate, magnesium stearate, solid polyethylene glycol, sodium dodecyl sulfate, or a mixture thereof. A buffering agent may be also comprised in capsule, tablet and pill preparations.

Solid preparations such as tablet, sugar pill, capsule, pill and granule can be prepared using a coating or shell, such as casing and other materials known in the art. Such preparations may comprise an opacifying agent, and the release of the active compound or the compound of the composition may be carried out in a certain part of digestive tract in a tardive manner. Embedding components such as polymeric materials and waxy materials may be employed herein. If necessary, the active compound may also be used to prepare a microcapsule with one or more of the above excipients.

Liquid preparations used for oral administration comprised pharmaceutically acceptable emulsion, solution, suspension, syrup or tincture. In addition to the active compound, the liquid preparations may also comprise an inert diluent conventionally used in the art, such as water or other solvents, solubilizer and emulsifier, including ethanol, isopropanol, ethyl carbonate, ethyl acetate, propylene glycol, 1,3-butanediol, dimethylformamide and oils, especially cottonseed oil, peanut oil, corn germ oil, olive oil, castor oil and sesame oil or a mixture thereof.

In addition to such inert diluents, the composition may also include an auxiliary, such as wetting agent, emulsifier, suspending agent, sweetener, corrigent and spice.

In addition to the active compound, the suspension may comprise a suspending agent, such as ethoxylated isostearyl alcohol, polyoxyethylene sorbitol and sorbitan ester, microcrystalline cellulose, aluminum methylate and agar or a mixture thereof.

The composition for parenteral injection may comprise a physiologically acceptable sterile aqueous or non-aqueous solution, dispersion, suspension or emulsion, and sterile powder for reconstitution into sterile injectable solutions or dispersions. Appropriate aqueous and non-aqueous carriers, diluents, solvents or excipients comprise water, ethanol, polyols and an appropriate mixture thereof.

Preparations of the compound of the present invention for topical administration comprise ointment, powder, patch, spray and inhalant. The active ingredient is mixed under sterile conditions with a physiologically acceptable carrier and any preservatives, buffering agents, or propellants which may be required if necessary.

The compound of the invention may be administered alone or in combination with other pharmaceutically-acceptable compounds. When the pharmaceutical composition is used, a safe and effective amount of the compound of the invention is administered to mammals (such as humans) who need treatment where an effective amount of a pharmaceutically-acceptable dosage is employed for administration. For a human of 60 kg body weight, a daily dosage is usually 0.2-1000 mg and preferably 0.5-500 mg. Certainly, other factors including administration routes and health of patients should also be taken into consideration for determining a specific dosage which is within the skill of the skilled physician.

Advantages of the present invention are described as follows.

(1) High liver delivery efficiency, active molecule is produced by the compound which can only be specifically catalyzed by CYP3A in the cytochrome P450 isozyme family in hepatocytes. The active molecule has a high negative charge and is not easily discharged outside the liver, so the concentration in the liver is higher, and the liver delivery effect is achieved.

(2) High activity, more drugs are present in the liver because of liver delivery, and antiviral activity can be greatly improved.

(3) Low side effects, the same amount of precursor drugs is rarely metabolized into active molecules outside the liver, so the toxicity to major organs such as kidneys and heart is greatly reduced.

The invention will be further illustrated below in conjunction with specific embodiments. It should be understood that these embodiments are merely used to describe the invention but not intended to limit the scope of the invention. In the following examples, the experimental methods of which the specific conditions are not specified, are usually carried out according to conventional conditions or the conditions recommended by the manufacturer. Unless otherwise specified, percentage and portion are calculated by weight.

Example 1: PA2001

Synthetic Route:

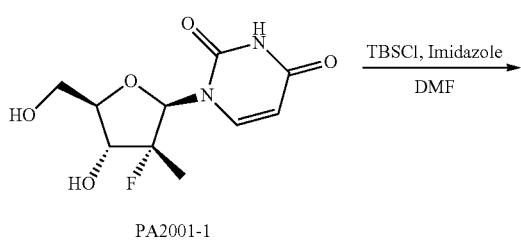

PA2001-1

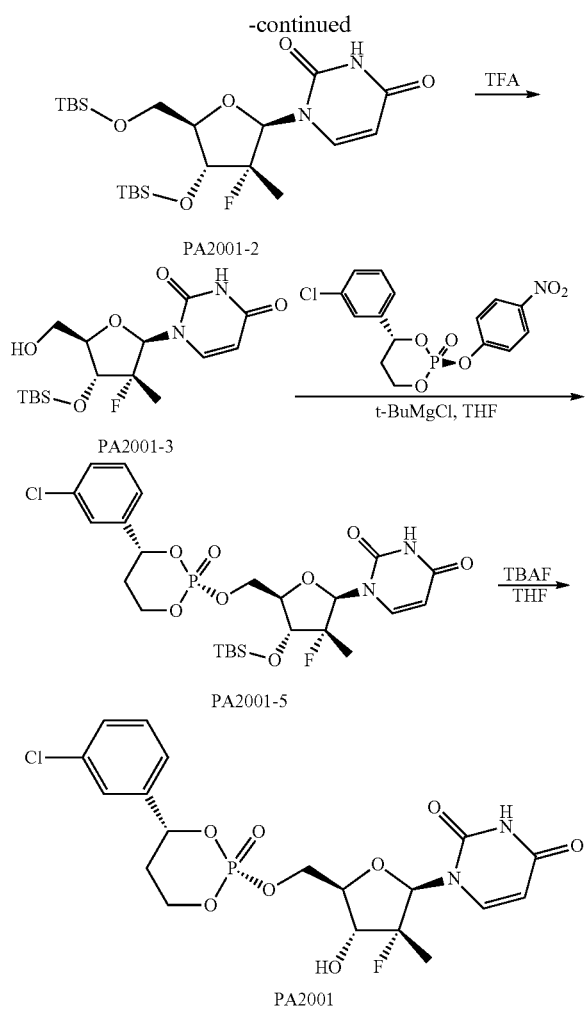

Experiment

Step (1) Synthesis of Compound PA2001-2

6.0 g (23.07 mmol) of compound PA2001-1 was added into a 250 mL eggplant-shaped flask to which 60 mL of DMF was added and stirred for complete dissolution. 9.4 g (138.46 mmol) of imidazole was added to the reaction system and dissolved under stirring. Then 13.85 g (92.30 mmol) of TBSCl was added, and the reaction mixture was stirred at room temperature overnight. When the compound PA2001-1 was confirmed by thin layer chromatography (TLC) (a mixture of PE and EA in a ratio of 2:1 was used as the mobile phase) to be absent, the reaction mixture was diluted with 50 mL of water and extracted three times with EA each for 150 mL. The three organic phases were combined and evaporated under rotation to remove the solvent. The resulting product was purified by column chromatography with an eluent of PE and EA at a volume ratio of 5:1 to obtain 11 g of a white solid product.

Step (2) Synthesis of Compound PA2001-3

3.0 g (6.16 mmol) of compound PA2001-2 was added to a 50 mL three-necked flask to which 6 mL of THF was added with a syringe. The reaction mixture was stirred at room temperature for complete dissolution. Then a mixture of 6 mL of TFA and 6 mL of THF was slowly dropwise added to the reaction mixture through a separatory funnel in an ice water bath under nitrogen protection. The reaction mixture was reacted under stirring at room temperature for 4 h. At this time, PA2001-2 was monitored by thin layer chromatography (TLC) (a mixture of PE and EA at a volume ratio of 2:1 was used as the mobile phase) to be present in a large amount, and 6 mL of TFA was added through a separatory funnel in an ice water bath. After the reaction was performed under stirring for 1 h, the ice water bath was removed and the reaction mixture was stirred at room temperature overnight, and a ratio of the target compound to the raw material was determined by TLC (a mixture of PE and EA at a volume ratio of 2:1 was used as the mobile phase) to be approximately 1:1. The reaction mixture was diluted with 50 mL of water and extracted with EA three times each of 120 mL. The three organic phases were collected and combined. The combined organic phase was evaporated under rotation to remove the solvent, and then was neutralized with 50 mL of saturated NaHCO$_3$ solution to adjust the pH to neutral. The neutralized product was extracted with EA three times each of 120 mL. Then the three organic phases were collected and combined. The combined organic phase was evaporated under rotation to remove the solvent. The resulting product was separated and purified using silica gel column chromatography with an eluent prepared by PE and EA at a volume ratio of 3:1 to obtain 2.0 g of a white solid product with a yield of 86%.

Step (3) Synthesis of Compound PA2001-5

1.7 g of compound PA2001-3 (4.5 mmol) and 10 mL of anhydrous THF were sequentially added to a 50 mL three-necked flask under the protection of nitrogen. After the nitrogen was replaced three times, the reaction mixture was cooled to about 0° C., and 6.4 mL of 1 M tert-butylmagnesium chloride was slowly added dropwise to the reaction mixture. After the reaction was performed under the protection of nitrogen for 1 h, 2 g of compound PA2001-4 (5.4 mmol) was added to the mixture in one batch, and the reaction mixture was naturally heated to room temperature and stirred overnight. After added with 20 mL of saturated ammonium chloride solution and stirred for 30 min, the reaction mixture was further added with 100 mL of EA, and washed three times with water each for 50 mL and washed with 50 mL of saturated brine once. The reaction mixture was evaporated at 45° C. under vacuum and rotation to remove the solvent and the resulting product was separated and purified using column chromatography with an eluent prepared by PE and EA at a volume ratio of 2:1 to obtain 954 mg of a white solid product with a yield of 35%.

Step (4) Synthesis of Compound PA2001

534 mg of compound PA2001-5 (0.88 mmol) was dissolved in 5 mL of tetrahydrofuran to produce a mixture, to which 2.6 mL of 1 M butyl ammonium fluoride tetrahydrofuran solution (2.6 mmol) containing 5% of water was added. The reaction mixture was stirred at room temperature for 20 min. After the reaction was demonstrated by TLC to be complete, the reaction mixture was diluted with 30 mL of water, extracted with ethyl acetate twice each of 50 mL. The two organic phases were collected and combined. The combined organic phase was dried with anhydrous Na$_2$SO$_4$ and desolventized under vacuum. The resulting product was separated and purified using silica gel column chromatography with an eluent prepared by PE and EA at a volume ratio of 1:1 to obtain a solid. And then the solid was purified again by Combiflash to obtain 35 mg of a white solid product with a yield of 25%.

Example 2: PA2020

Synthetic Route:

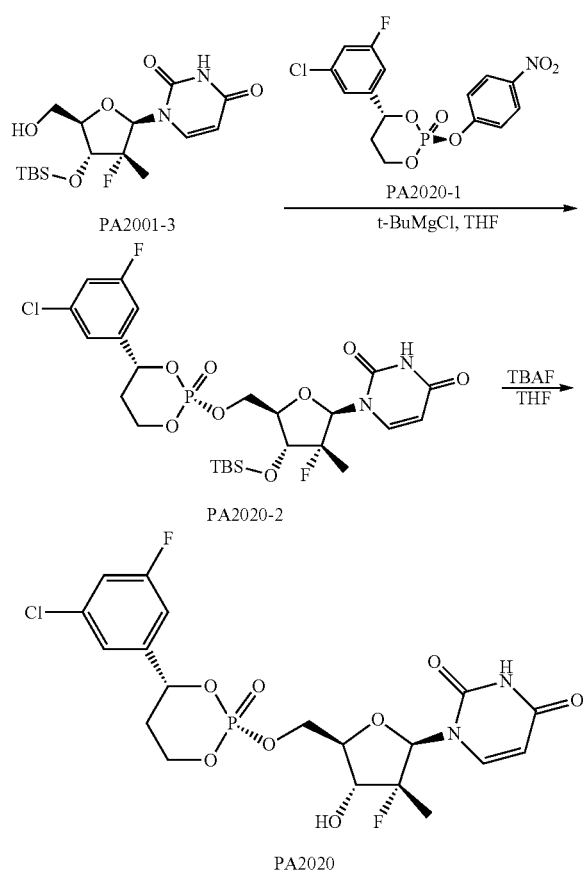

Experiment

Step (1) Synthesis of Compound PA2020-2

1.7 g (4.51 mmol) of compound PA2001-3 and 10 mL of anhydrous THF were sequentially added to a 50 mL three-necked flask under the protection of nitrogen. After the nitrogen was replaced three times, the reaction mixture was cooled to about 0° C. The mixture of 10.2 mL of BuMgCl (1.7N) and 20 mL of anhydrous THF were added dropwise, and after sharing 10 minutes, the addition is completed. After the reaction was performed under the protection of nitrogen for 30 min, 1.75 g of compound PA2020-1 (4.51 mmol) was added to the mixture in one batch, and the reaction mixture was heated to room temperature and stirred overnight. After added 100 mL of saturated ammonium chloride solution and stirred for 30 min, the reaction mixture was further added with 200 mL of EA, and washed three times with water each for 50 mL, and washed with 50 mL of saturated brine once. The reaction mixture was evaporated at 45° C. under vacuum and rotation to remove the solvent, and the resulting product was separated and purified using chromatography column to obtain 678 mg of a brown solid product with a yield of 20%, where the eluents were sequentially PE, a mixture of PE and EA at a volume ratio of 2:1, a mixture of PE and EA at a volume ratio of 1:1 and EA.

Step (2) Synthesis of Compound PA2020

270 mg of compound PA2020-2, 5 mL of THF and 1 mL of THF(1N) in TBAF were sequentially added to a 25 mL mouton-necked flask. After the reaction mixture was stirred at room temperature for 10 min, the reaction mixture was further added with 100 mL of DCM, and washed three times with water each for 30 mL, and washed with 30 mL of saturated brine once. The reaction mixture was evaporated at 40° C. under vacuum and rotation to remove the solvent, and the resulting product was separated and purified using chromatography column DCM to obtain an off-white solid, where the eluents were sequentially DCM and mixtures of DCM and MeOH at a volume ratio of 50:1, 40:1, 30:1 and 20:1. And then the resulting product was purified again by Combiflash and lyophilized to obtain 146 mg of a white solid.

Example 3: PA2024

Synthetic Route:

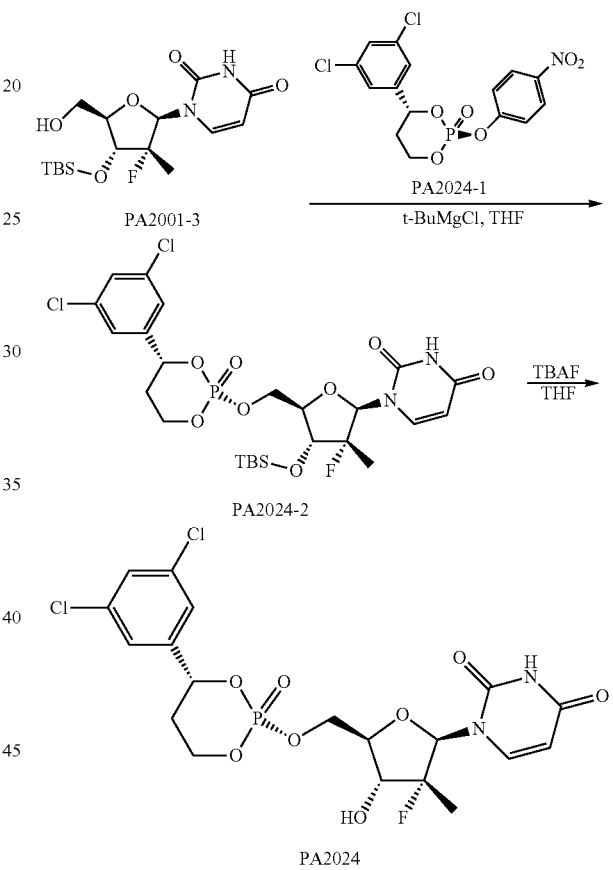

Experiment

Step (1) Synthesis of Compound PA2024-2

440 mg of compound PA2001-3 (1.06 mmol) was dissolved in 30 mL of tetrahydrofuran under the protection of nitrogen. When the temperature was cooled to about 0° C. by an ice water bath, 3.2 mL of 1.7 M tert-butylmagnesium chloride (5.44 mmol, 5 eq) was slowly dropwise added. After the addition was completed, the reaction solution was stirred at room temperature for 1 h. The temperature was cooled to about 0° C. again and then 500 mg (1.24 mmol) of compound PA2024-1 was added. The reaction mixture was stirred at room temperature overnight. After quenching with 30 mL of saturated aqueous ammonium chloride, the reaction mixture was extracted with ethyl acetate twice each of 60 mL. The two organic phases were collected and combined. The combined organic phase was dried with anhydrous $Na_2SO_4$ and desolventized under vacuum. The resulting product was separated and purified using silica gel column chromatography with an eluent prepared by PE and EA at a volume ratio of 1:1 to 1:4 to obtain 115 mg of a brownish yellow solid product with a yield of 15%.

Step (2) Synthesis of Compound PA2024

100 mg of compound PA2024-2 (0.15 mmol) was dissolved in 5 mL of tetrahydrofuran to produce a mixture, to which 0.5 mL of 1M butyl ammonium fluoride tetrahydrofuran solution (0.5 mmol) containing 5% of water was added. The reaction mixture was stirred at room temperature for 2 h. After the reaction was demonstrated by TLC to be complete, the reaction mixture was diluted with 50 mL of water, extracted with ethyl acetate twice each of 30 mL. The two organic phases were collected and combined. The combined organic phase was dried with anhydrous $Na_2SO_4$ and desolventized under vacuum. The resulting product was separated and purified using silica gel column chromatography with an eluent prepared by EA and MeOH at a volume ratio of 20:1 to 10:1 to obtain a solid, which was purified again by Combiflash to obtain 35 mg of a light white solid with a yield of 53%.

Example 4: PA2025

Synthetic Route:

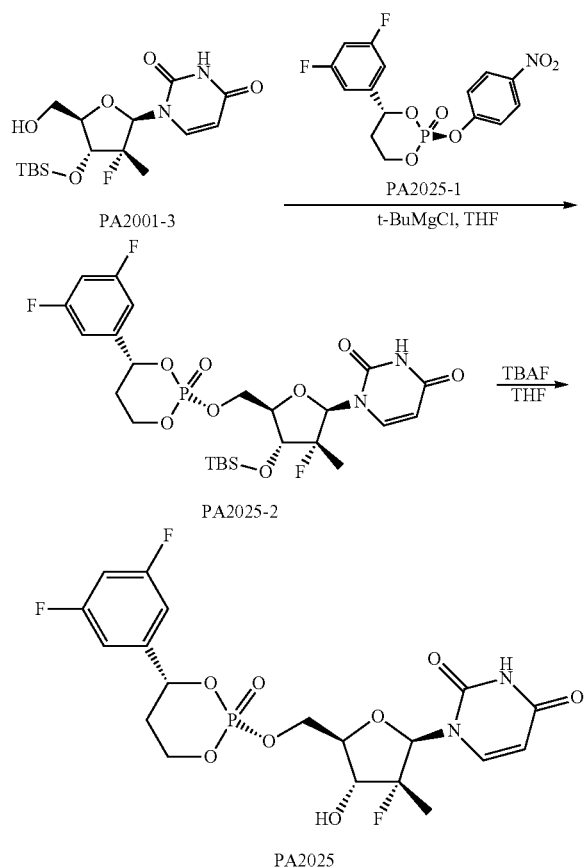

Experiment

Step (1) Synthesis of Compound PA2025-2

200 mg of compound PA2001-3 (0.53 mmol) and 5 mL of anhydrous THF were sequentially added to a 25 mL three-necked flask under the protection of nitrogen. After the nitrogen was replaced three times, the reaction mixture was cooled to about 0° C., and 1.2 mL of BuMgCl (1.7N) and 3 mL of anhydrous THF were dropwise added to the reaction mixture, and after sharing 5 min, the addition is completed. After the reaction was performed under the protection of nitrogen for 30 min, 196.6 mg of compound PA2025-1 (0.53 mmol) was added to the mixture in one batch, and the reaction mixture was naturally heated to room temperature and stirred overnight. After added with 50 mL of saturated ammonium chloride solution and stirred for 30 min, the reaction mixture was further added with 100 mL of EA, and washed three times with water each for 30 mL, and washed with 30 mL of saturated brine once. The reaction mixture was evaporated at 45° C. under vacuum and rotation to remove the solvent and the resulting product was separated and purified using chromatography column to obtain 151 mg of a brown solid product with a yield of 46%, where the eluents were sequentially PE, mixtures of PE and EA respectively at a volume ratio of 2:1 and 1:1 and EA.

Step (2) Synthesis of Compound PA2025

150 mg of compound PA2025-2, 4 mL of THF and 1 mL of THF in TBAF were sequentially added to a 25 mL single mouth flask. The reaction mixture was stirred at room temperature for 2 h. 100 mL of DCM was further added to the mixture, and the reaction mixture was washed three times with water each for 30 mL, and washed with 30 mL of saturated brine once. The reaction mixture was evaporated at 40° C. under vacuum and rotation to remove the solvent and the resulting product was separated and purified using chromatography column to obtain an off-white solid, where the eluents were sequentially DCM and mixtures of DCM and MeOH respectively at a volume ratio of 50:1, 40:1, 30:1 and 20:1. And then the solid was purified again by Combiflash and lyophilized to obtain 39 mg of a white solid.

Example 5: PA2026

Synthetic Route:

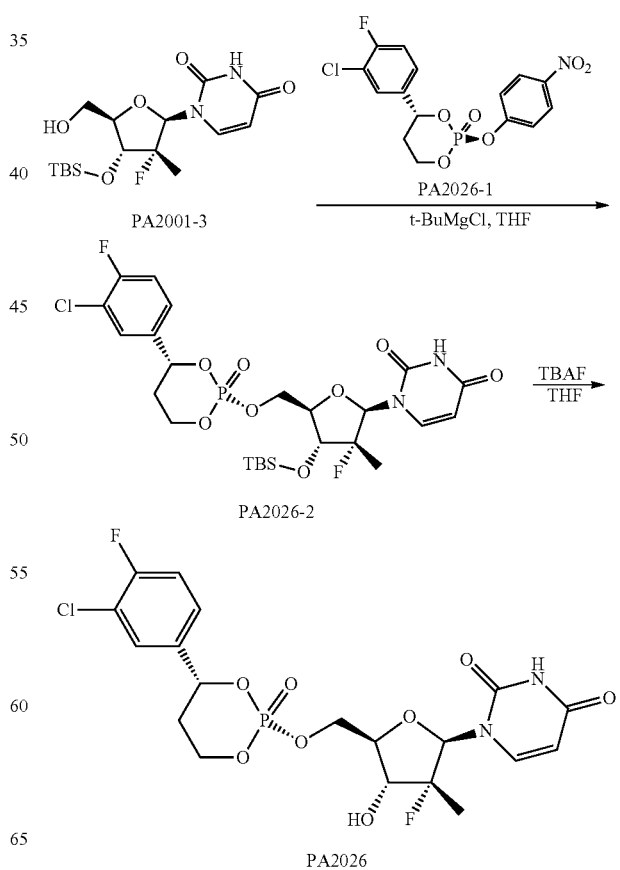

Experiment

Step (1) Synthesis of Compound PA2026-2

200 mg of compound PA2001-3 (0.53 mmol) was dissolved in 10 mL of tetrahydrofuran under the protection of nitrogen which the operating environment anhydrous and oxygen-free. After the reaction mixture was cooled to about 0° C. by an ice water bath, 1.2 mL of 1.7 M tert-butylmagnesium chloride (2.04 mmol) was slowly added dropwise to the reaction mixture. After the addition was completed, the reaction mixture was stirred at room temperature for 1 h. The temperature was cooled to about 0° C. again and then 249 mg of compound PA2026-1 (0.64 mmol) was added. The reaction mixture was stirred at room temperature overnight. After quenched with 30 mL saturated aqueous ammonium chloride, the reaction mixture was extracted with ethyl acetate twice each of 60 mL. The two organic phases were collected and combined. The combined organic phase was dried with anhydrous Na$_2$SO$_4$ and desolventized under vacuum. The resulting product was separated and purified by column chromatography with an eluent of PE and EA at a volume ratio of 1:1 to 1:3 to obtain 193 mg of a brownish yellow solid product with a yield of 57%.

Step (2) Synthesis of Compound PA2026

193 mg of compound PA2026-2 (0.31 mmol) was dissolved in 5 mL of tetrahydrofuran produce a mixture, to which 1 mL of 1M butyl ammonium fluoride tetrahydrofuran solution (1 mmol) containing 5% of water was added. The reaction mixture was stirred at room temperature for 2 h. After the reaction was demonstrated by TLC to be complete, the reaction mixture was diluted with 50 mL of water, extracted with ethyl acetate twice each of 30 mL. The two organic phases were collected and combined. The combined organic phase was dried with anhydrous Na$_2$SO$_4$ and desolventized under vacuum. The resulting product was separated and purified using silica gel column chromatography with an eluent prepared by EA and MeOH at a volume ratio of 20:1 to 10:1 to obtain a solid of compound PA2026. And then the solid was purified again by Combiflash to obtain 56 mg of a light white solid with a yield of 35%.

Example 6: PA2027

Synthetic Route:

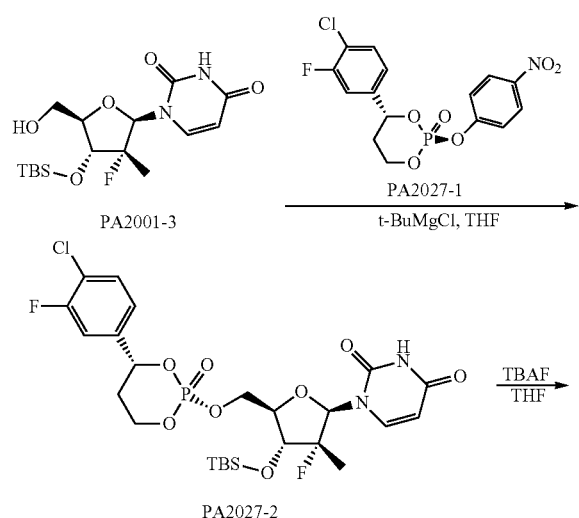

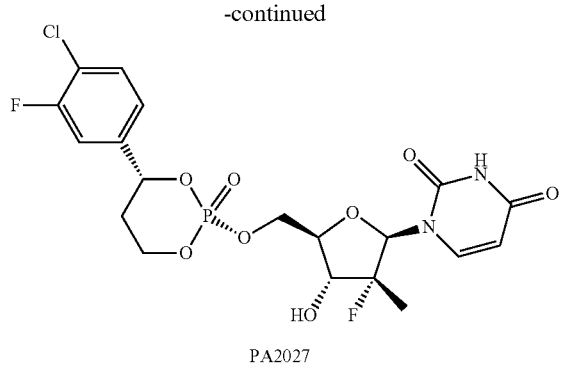

PA2027

Experiment

Step (1) Synthesis of Compound PA2027-2

176 mg of compound PA2001-3 (0.47 mmol) and 4 mL of anhydrous THF were sequentially added to a 25 mL three-necked flask under the protection of nitrogen. After the nitrogen was replaced three times, the reacting mixture was cooled to about 0° C., and 0.92 mL of BuMgCl (1.56 mmol) was slowly added dropwise to the reaction mixture, and after sharing 5 min, the addition is completed. After the reaction was performed under the protection of nitrogen for 30 min, 150 mg of compound PA2027-1 (0.39 mmol) was added to the mixture in one batch, and the reaction mixture was naturally heated to room temperature and stirred overnight. After added with 5 mL of saturated ammonium chloride solution and stirred for 30 min, the reaction mixture was further added with 10 mL of water, and extracted with EA three times each of 30 mL, and washed with 10 mL of saturated brine once. The reaction mixture was evaporated at 45° C. under vacuum and rotation to remove the solvent and the resulting product was separated and purified using chromatography column to obtain 55 mg of a brown solid product with a yield of 23%, where the eluents were sequentially PE, mixtures of PE and EA respectively at a volume ratio of 2:1 and 1:1 and EA Step (2) Synthesis of Compound PA2027

50 mg of compound PA2027-2, 2 mL of THF and 1.9 mL of THF in TBAF were sequentially added to a 25 mL single mouth flask. The reaction mixture was stirred at room temperature for 10 min, and the 10 mL of EA was further added, and the reaction mixture was washed sequentially with 10 mL of water and 10 mL of saturated brine. The reaction mixture was evaporated at 45° C. under vacuum and rotation to remove the solvent and the resulting product was separated and purified using chromatography column DCM to obtain a white solid, where the eluents were sequentially DCM and mixtures of DCM and MeOH respectively at a volume ratio of 50:1, 40:1, 30:1 and 20:1. And then the solid was purified again by Combiflash and lyophilized to obtain 8 mg of a white solid.

Example 7: PA2028

Synthetic Route:

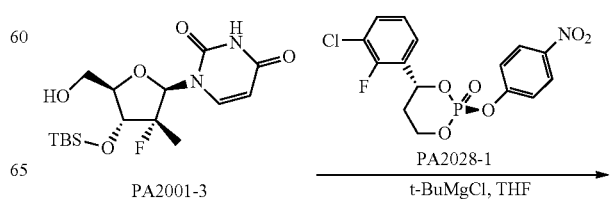

-continued

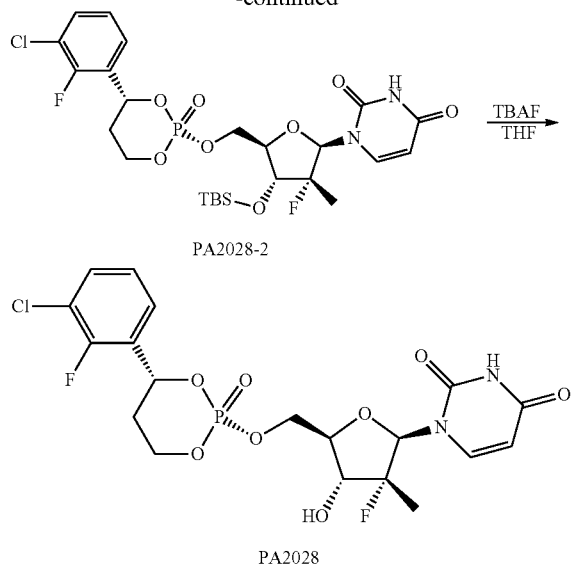

PA2028-2

PA2028

Experiment

Step (1) Synthesis of Compound PA2028-2

400 mg of compound PA2001-3 (1.03 mmol) was dissolved in 30 mL of tetrahydrofuran under the protection of nitrogen, i.e., an anhydrous and oxygen-free environment. After the reaction mixture was cooled to about 0° C. by an ice water bath, 4.2 mL of 1 M tert-butylmagnesium chloride (4.2 mmol, 3.9 eq) was slowly added dropwise to the reaction mixture. After the addition was completed, the reaction mixture was stirred at room temperature for 1 h. The temperature was cooled to about 0° C. again and then 430 mg of compound PA2028-1 (1.1 mmol) was added. The reaction mixture was stirred at room temperature overnight. After quenched with 30 mL saturated aqueous ammonium chloride, the reaction mixture was extracted with ethyl acetate twice each of 60 mL. The two organic phases were collected and combined. The combined organic phase was dried with anhydrous Na$_2$SO$_4$ and desolventized under vacuum. The resulting product was separated and purified using silica gel column chromatography with an eluent prepared by PE and EA at a volume ratio of 1:1 to 1:3 to obtain 134 mg of a brownish yellow solid product with a yield of 20%.

Step (2) Synthesis of Compound PA2028

130 mg of compound PA2028-2 (0.2 mmol) was dissolved in 5 mL of tetrahydrofuran to produce a mixture, to which 0.45 mL of 1M butyl ammonium fluoride tetrahydrofuran solution (0.45 mmol) containing 5% of water was added. The reaction mixture was stirred at room temperature for 2 h. After the reaction mixture was demonstrated by TLC to be complete, the reaction mixture was diluted with 50 mL of water, extracted with ethyl acetate twice each of 30 mL. The two organic phases were collected and combined. The combined organic phase was dried with anhydrous Na$_2$SO$_4$ and desolventized under vacuum. The resulting product was separated and purified using silica gel column chromatography with an eluent prepared by EA and MeOH at a volume ratio of 20:1 to 10:1 to obtain a solid of compound PA2028. And then the solid was purified again by Combiflash to obtain 50 mg of a light white solid with a yield of 53%.

Example 8: PA2029

Synthetic Route:

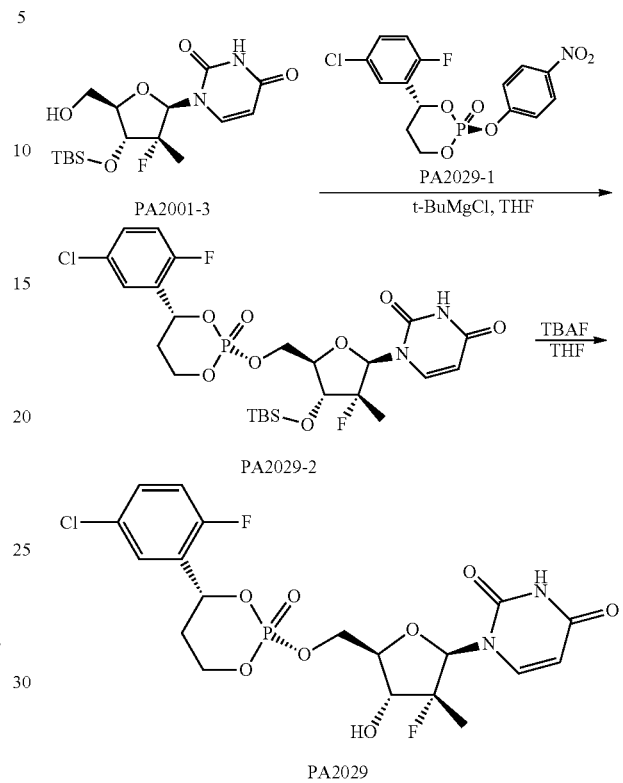

PA2029

Experiment

Step (1) Synthesis of Compound PA2029-2

500 mg of compound PA2001-3 (1.34 mmol) was added to a 50 mL three-necked flask, to which 5 mL of anhydrous THF was added with a syringe under nitrogen protection and ice water bath conditions. The reaction mixture was stirred for complete dissolution, and then 5.1 mL of 1 M tert-butylmagnesium chloride (5.08 mmol) was slowly added dropwise to the reaction mixture by a syringe. After the completion of the dropwise addition, the reaction solution was stirred under an ice bath for 0.5 h, and the ice water bath was removed, and the reaction mixture was further stirred at room temperature for 1 h. At this time, the reaction mixture turned white to a slightly yellow paste and 620 mg of compound PA2029-1 (1.60 mmol) was added in one batch, and the reaction mixture was stirred at room temperature overnight. When the compound PA2029-1 was confirmed by thin layer chromatography (TLC) (a mixture of PE and EA in a ratio of 1:1 was used as the mobile phase) to be absent, the reaction mixture was quenched with 40 mL saturated aqueous ammonium chloride and extracted with EA three times each of 100 mL. The three organic phases were collected and combined and evaporated under rotation to remove the solvent. The resulting product was purified by column chromatography with an eluent of PE and EA at a volume ratio of 2:1 to obtain 367 g of a brown solid product with a yield of 44%.

Step (2) Synthesis of Compound PA2029

376 mg of compound PA2029-2 (0.59 mmol) placed was added in a 100 mL eggplant-shaped flask, to which 4 mL of anhydrous THF was added with a syringe, and stirred at room temperature until complete dissolution. 1 mL (1 mmol) of TBAF was added to the reaction mixture by a syringe. The reaction mixture was further stirred at room temperature for 2 h. When the raw material was confirmed by thin layer chromatography (TLC) (a mixture of DCM and MeOH in a ratio of 10:1 was used as the mobile phase) to be absent, the reaction mixture was diluted with 40 mL of water and extracted three times with EA each for 50 mL. The three organic phases were combined and evaporated under rotation to remove the EA. The resulting product was purified by column chromatography with an eluent of DCM and MeOH at a volume ratio of 20:1 to obtain a white solid. And then the resulting product purified again by Combiflash to obtain 139 mg of a white solid.

TABLE 1

Compounds prepared in examples

| Number | Structural formula | Molecular weight |
| --- | --- | --- |
| PA2001 | | 490.80 |
| PA2020 | | 508.79 |
| PA2024 | | 525.25 |
| PA2025 | | 492.34 |

TABLE 1-continued

Compounds prepared in examples

| Number | Structural formula | Molecular weight |
|---|---|---|
| PA2026 | (4-fluoro-3-chlorophenyl cyclic phosphate of 2'-deoxy-2'-fluoro-2'-methyluridine) | 508.79 |
| PA2027 | (4-chloro-3-fluorophenyl cyclic phosphate of 2'-deoxy-2'-fluoro-2'-methyluridine) | 508.79 |
| PA2028 | (3-chloro-2-fluorophenyl cyclic phosphate of 2'-deoxy-2'-fluoro-2'-methyluridine) | 508.79 |
| PA2029 | (5-chloro-2-fluorophenyl cyclic phosphate of 2'-deoxy-2'-fluoro-2'-methyluridine) | 508.79 |

TABLE 2

NMR data of the compounds prepared in the examples

| Number | NMR data |
|---|---|
| PA2001 | $^1$H NMR (400 MHz, DMSO-d$_6$) δ 11.52 (s, 1H), 7.57-7.46 (m, 2H), 7.45-7.34 (m, 3H), 6.13-5.80 (m, 2H), 5.78-5.64 (m, 1H), 5.51 (d, J = 8.1 Hz, 1H), 4.61-4.27 (m, 4H), 4.00 (s, 1H), 3.80 (s, 1H), 2.29-2.12 (m, 2H), 1.23 (d, J = 22.6 Hz, 3H) ppm. |
| PA2020 | $^1$H NMR (400 MHz, CDCl$_3$) δ 8.59 (s, 1H), 7.49 (d, J = 8.2 Hz, 1H), 7.18 (s, 1H), 7.13 (dt, J = 8.3, 2.1 Hz, 1H), 7.03 (d, J = 8.8 Hz, 1H), 6.30-6.12 (m, 1H), 5.74-5.63 (m, 2H), 4.81-4.45 (m, 4H), 4.14 (d, J = 9.4 Hz, 1H), 4.04-3.91 (m, 1H), 3.37 (s, 1H), 2.40-2.12 (m, 2H), 1.46 (d, J = 22.6 Hz, 3H) ppm. |
| PA2024 | $^1$H NMR (400 MHz, DMSO-d$_6$) δ 11.52 (s, 1H), 7.62 (d, J = 1.8 Hz, 1H), 7.53-7.49 (m, 3H), 6.15-5.87 (m, 2H), 5.75 (d, J = 5.2 Hz, 1H), 5.55 (d, J = 8.1 Hz, 1H), 4.62-4.31 (m, 4H), 4.02 (s, 1H), 3.90-3.72 (m, 1H), 2.25-2.21 (s, 2H), 1.26 (d, J = 22.6 Hz, 3H) ppm. |

TABLE 2-continued

NMR data of the compounds prepared in the examples

| Number | NMR data |
|---|---|
| PA2025 | $^1$H NMR (400 MHz, CDCl$_3$) δ 8.60 (s, 1H), 7.49 (d, J = 8.2 Hz, 1H), 6.96-6.81 (m, 3H), 6.21 (d, J = 16.6 Hz, 1H), 5.72-5.65 (m, 2H), 4.80-4.43 (m, 4H), 4.14 (d, J = 9.3 Hz, 1H), 4.03-3.97 (m, 1H), 3.03-2.95 (m, 1H), 2.39-2.25 (m, 1H), 2.22-2.13 (m, 1H), 1.45 (d, J = 14.7, 10.4 Hz, 3H) ppm. |
| PA2026 | $^1$H NMR (400 MHz, CDCl$_3$) δ 8.33 (s, 1H), 7.53-7.44 (m, 2H), 7.27-7.18 (m, 2H), 6.23 (d, J = 19.8 Hz, 1H), 5.71-5.66 (m, 2H), 4.78-4.72 (m, 1H), 4.66-4.47 (m, 3H), 4.13 (d, J = 9.6 Hz, 1H), 4.03-3.91 (m, 1H), 3.39-3.30 (m, 1H), 2.41-2.32 (m, 1H), 2.20-2.13 (m, 1H), 1.50-1.43 (m, 3H) ppm. |
| PA2027 | $^1$H NMR (400 MHz, CDCl$_3$) δ 8.54 (s, 1H), 7.52-7.43 (m, 2H), 7.22 (dd, J = 9.6, 2.0 Hz, 1H), 7.11 (d, J = 8.3 Hz, 1H), 6.22 (d, J = 19.3 Hz, 1H), 5.75-5.64 (m, 2H), 4.80-4.45 (m, 4H), 4.14-4.12 (m, 1H), 3.99 (d, J = 21.9 Hz, 1H), 3.18 (s, 1H), 2.40-2.27 (m, 1H), 2.19-2.12 (m, 1H), 1.46 (d, J = 22.6 Hz, 3H) ppm. |
| PA2028 | $^1$H NMR (400 MHz, CDCl$_3$) δ 8.76 (s, 1H), 7.55-7.34 (m, 3H), 7.19 (dt, J = 8.9, 4.4 Hz, 1H), 6.22 (d, J = 18.1 Hz, 1H), 5.95 (d, J = 11.2 Hz, 1H), 5.70 (t, J = 6.8 Hz, 1H), 4.77 (tt, J = 12.0, 2.8 Hz, 1H), 4.70-4.45 (m, 3H), 4.15-4.11 (m, 1H), 3.99 (dd, J = 22.5, 9.4 Hz, 1H), 2.42-2.30 (m, 1H), 2.06-2.05 (m, 1H), 1.45 (d, J = 22.8 Hz, 3H) ppm. |
| PA2029 | $^1$H NMR (400 MHz, CDCl$_3$) δ 8.28 (s, 1H), 7.63-7.44 (m, 2H), 7.35 (ddd, J = 8.7, 4.5, 2.5 Hz, 1H), 7.12-7.04 (m, 1H), 6.24 (d, J = 20.0 Hz, 1H), 5.94 (d, J = 11.0 Hz, 1H), 5.72 (dd, J = 8.2, 2.2 Hz, 1H), 4.81-4.45 (m, 4H), 4.15 (dd, J = 9.3, 1.8 Hz, 1H), 3.99 (dd, J = 21.2, 9.1 Hz, 1H), 3.34 (s, 1H), 2.38-2.22 (m, 2H), 1.52-1.44 (m, 3H) ppm. |

Example 9: Evaluation of Human Liver Microsomal Metabolism In Vitro

Test Methods

The human liver microsome (HLM) used in this test was purchased from In Vitro Technologies (IVT) with a batch number of SSP X008070, which was a mixed liver microsome extracted from the liver tissues of 150 donors. The product description recorded that the metabolic activity of CYP3A4 in this batch of the human liver microsomes was 1.734 nmol/mg/min (the rate at which testosterone is metabolized to produce 6-β testosterone). The test compound was synthesized by Zhejiang Plato Pharmaceutical Technology Co., Ltd., and dissolved in methanol to prepare a storage solution having a concentration of 25 mM. The enzymatic reaction was carried out in a 100 mM KH2PO4 buffer solution (pH 7.4) at a test compound concentration of 25 μM and a human liver microsome concentration of 2 mg/ml. The reaction was initiated by the addition of NADPH (final concentration 2 mM). After reacting for 5 min in a constant temperature shaking water bath, the reaction was terminated by the rapid addition of methanol at a volume of 1.5 times that of the reaction mixture. The reaction solution was centrifuged at a maximum speed of 13,600 rpm using an Eppendorf bench top centrifuge for 20 min, and the supernatant was taken. And then the supernatant was dried by a nitrogen blower and redissolved in mobile phase A (aqueous solution containing 5 mM ammonium acetate and 0.05% formic acid v/v). The resulting sample was analyzed by LC-MS/MS (Waters, Acquity UPLC HSS T3 column).

TABLE 3

Release rate of monophosphate product 2FM-UMP in the in vitro metabolism of the compounds by human liver microsomes

| Number | Configuration | Activating rate pmol/min/mg HLM |
|---|---|---|
| PA2001 | cis S-configuration | 6.80 |
| PA2020 | cis S-configuration | 22.8 |
| PA2024 | cis S-configuration | 22.2 |
| PA2025 | cis S-configuration | 8.17 |
| PA2026 | cis S-configuration | 7.06 |
| PA2027 | cis S-configuration | 5.36 |
| PA2028 | cis S-configuration | 11.7 |
| PA2029 | cis S-configuration | 28.2 |

Notes:
cis S-configuration: unless otherwise specified, it indicated that C4 was the S-configuration in the phosphate ring structure, and a relative stereochemistry of P2 and C4 is cis.

Result analysis: the compound can be activated in vitro by human liver microsomes into a monophosphate metabolite 2FM-UMP, metabolic rate varied among different compounds. It was surprisingly found that the transformation rate of PA2029, PA2020 and PA2024 was much higher than other candidate compounds, and almost more than twice that of other candidate compounds (Table 3). Therefore, PA2029, PA2020 and PA2024 were selected to further investigate the tissue distribution characteristics of their monophosphate (2FM-UMP) and triphosphate (2FM-UTP) metabolites after orally administered to rats.

Example 12: Compound Tissue Distribution Experiment 12.1 Method 12.1.1 Animal Experiment Sprague Dawley rats, male, weighing 180-300 g, were provided by Shanghai Xipuer-Beikai Experimental Animal Co., Ltd. Male animals were allowed to adapt to the environment for more than 3 days, and fasted for 12 hours before the experiment, but were free to drink water. PA2020, PA2024, PA2029 and sofosbuvir were respectively dissolved in a mixed solvent of Cremophor EL, ethanol and normal saline at a volume ratio of 10:10:80 to prepare corresponding solutions. Before the administration, the animals' weight was checked to determine whether the rats met the experimental requirements. Twelve rats were selected for grouping, 2 rats in each group, and 30 mg/kg of a drug solution was administered intragastrically to the rats. Samples were respectively collected at 0.5 h, 1 h, 3 h, 6 h, 12 h and 24 h after the administration. After the rats were euthanized with carbon dioxide, the blood was collected from the heart and stored in heparin anticoagulation tubes. The blood was centrifuged at 6,000 rpm and 4° C. for 5 min, and the supernatant plasma was taken and stored in dry ice. The kidney, liver and heart of the rats were collected and rinsed with normal saline pre-cooled at 4° C. and stored in dry ice after the water was drained. After the experiment, the samples were stored in a −80° C. refrigerator.

12.1.2. Determination of Metabolites 2FM-UR, 2FM-UMP and 2FM-UTP Coming from Dephosphoric Acid, Monophosphate and Triphosphate Respectively in Biological Samples Due to the difference in polarity, 2FM-UR, 2FM-UMP and 2FM-UTP were separated and detected using different methods, so that the used LC-triple quadrupole mass spectrometry detectors, the pretreatment conditions, chromatographic and mass spectrometric conditions varied among these compounds.

Preparation of 2FM-UR Sample

Plasma Sample

In the ice bath, 50 μL of plasma was first mixed with 50 μL of internal standard solution (10% trichloroacetic acid solution of tenofovir at 500 ng/mL). After centrifugation at 13,000 rpm and 4° C. for 10 min, 20 μL of the supernatant was mixed with 180 μL of water, and 5 μL of the resulting solution was injected and analyzed by LC-MS/MS.

The kidney, liver and heart tissue were mixed with a buffer in a volume ratio of 1:5 and fully disrupted in the ice bath. 20 μL of the tissue homogenate was mixed with 20 μL of the internal standard solution (500 ng/mL of tenofovir in 10% trichloroacetic acid solution). After centrifugation at 13,000 rpm for 10 min at 4° C., 20 μL of the supernatant was mixed with 180 μL of water, and 5 μL of the resulting solution was injected and analyzed by LC-MS/MS.

Conditions of 2FM-UR Chromatographic Mass Spectrometry

LC-MS/MS-AJ (Triple Quad 5500, AB SCIEX) was used for sample analysis. Column: Acquity UPLC HSS T3 (2.1× 50 mm, 1.84); column temperature: 40° C.; flow rate: 0.5 mL/min. Mobile phase A: 0.1% aqueous formic acid, mobile phase B: acetonitrile solution. The sample was separated by gradient elution and the procedure was shown in Table 4. Mass spectrometry conditions corresponding to the internal standard: electrospray ionization (ESI) positive ion mode, multiple reaction monitoring (MRM) monitoring ion pair m/z: 288/176 (tenofovir), 261/113 (2FM-UR); the temperature was 500° C.; the scanning time was 0.03 s; the collision energy was 15V.

TABLE 4

| 2FM-UR liquid phase elution gradient conditions | |
| --- | --- |
| Time (min) | Mobile phase B (%) |
| Initial | 1 |
| 1.1 | 10 |
| 2.5 | 1 |

Preparation of 2FM-UMP Sample

Plasma Sample

In the ice bath, 30 μL of plasma was first mixed with 30 μL of internal standard solution (5% trichloroacetic acid solution of 100 ng/mL tolbutamide). After centrifugation at 13,000 rpm for 10 min at 4° C., 40 μL of the supernatant was mixed with 80 μL of water, and 5 μL of the injection was analyzed.

Kidney, liver, heart tissue: in the ice bath, tissue and 5 volumes of homogenization buffer of organ tissues (1.75 mL of methanol, 5 μL of 50% KOH solution and 0.75 mL of 268 mM EDTA solution, pH=8) were fully disrupted and mixed. 60 μL of tissue homogenate was mixed with 60 μl of internal standard solution (5% trichloroacetic acid solution of 100 ng/mL tolbutamide). After centrifugation at 13,000 rpm for 10 minutes at 4° C., 40 μL of the supernatant was mixed with 80 μL of water, and 5 μL of the injection was analyzed.

Conditions of 2FM-UMP Chromatographic Mass Spectrometry

LC-MS/MS-AJ (Triple Quad 5500, AB SCIEX) was used for sample analysis. Column: ACE 3 AQ (2.1×50 mm); column temperature: 55° C.; flow rate: 0.45 mL/min. Mobile phase A: 1.5% aqueous formic acid, mobile phase B: 1.5% formic acid acetonitrile solution. The sample was separated by gradient elution and the procedure was shown in Table 5. The peak times of 2FM-UMP and the corresponding internal standard tolbutamide were 1.02 and 2.42 min, respectively. Mass spectrometry condition: electrospray ionization (ESI) anion, multiple reaction monitoring (MRM) monitoring ion pair m/z: 339.2/79.0 (2FM-UMP), 269.0/169.8 (toluene).

TABLE 5

| 2FM-UMP liquid phase elution gradient conditions | |
| --- | --- |
| Time (min) | Mobile phase B (%) |
| Initial | 2 |
| 0.8 | 2 |
| 1.5 | 50 |
| 2 | 95 |
| 3 | 95 |
| 3.01 | 2 |
| 3.5 | 2 |

Preparation of 2FM-UTP Sample

Plasma sample: in the ice bath, 30 μL of plasma was first mixed with 30 μL of buffer (20 mM aqueous ammonium acetate solution, pH=8.0), and then was mixed with 120 μL of internal standard solution (200 ng/mL tolbutamide and 40 mM DBBA methanol solution). After centrifugation at 13,000 rpm for 10 minutes at 4° C., 60 μL of the supernatant was mixed with 60 µL of water, and 10 µL of the resulting solution was injected and analyzed.

Kidney, liver, heart tissue: in the ice bath, tissue and 5 volumes of homogenization buffer of organ tissues (1.75 mL of methanol, 5 µL of 50% KOH solution and 0.75 mL of 268 mM EDTA solution, pH=8) were fully disrupted and mixed. 30 µL of tissue homogenate was mixed with 30 µL of 20 mM ammonium acetate solution (pH=8.0) and then 120 µL of internal standard solution (200 ng/mL tolbutamide and 40 mM DBBA methanol solution) was mixed with the mixture. After centrifugation at 13,000 rpm for 10 minutes at 4° C., 60 µL of the supernatant was mixed with 60 µL of water, and 10 µL of the resulting solution was injected and analyzed.

Conditions of 2FM-UTP Chromatographic Mass Spectrometry

LC-MS/MS (API 4000, AB SCIEX) was used for sample analysis. Column: Agilent ZORBAxExtend-C18 (2.1×50 mm, 5 µm); Mobile phase A: 0.001% ammonia and 0.18 mM DBAA, mobile phase B: 10 mM DMHA and 3 mM ammonium acetate acetonitrile/water solution with the volume ratio was 50:50. The sample was separated by gradient elution and the procedure is shown in Table 6. The flow rate was 0.4 mL/min. The peak times of 2FM-UTP and the corresponding internal standard tolbutamide were 1.98 and 3.10 min, respectively. Mass spectrometry condition: electrospray ionization (ESI) anion, multiple reaction monitoring (MRM) monitoring ion pair m/z: 498.7/158.7 (2FM-UTP), 269.0/169.8 (toluene).

TABLE 6

LC gradient elution conditions for 2FM-UTP

| Time (min) | Mobile phase B (%) |
| --- | --- |
| 0 | 2 |
| 0.3 | 2 |
| 2 | 35 |
| 2.5 | 95 |
| 3.2 | 95 |
| 3.21 | 2 |
| 4.5 | 2 |

12.1.3. Data Analysis

The concentration of the metabolites of each compound in the liver was plotted as a column in response to time. The area under the tissue concentration-time curve ($AUC_{0-t}$) of 2FM-UR, 2FM-UMP, and 2FM-UTP was fitted to the calculation by using the Log-linear trapezoidal method in non-compartmental model of WinNonLin6.2.1 (Pharsight, CA). The liver-kidney ratio of 2FM-UMP and 2FM-UTP was their ratio of $AUC_{0-t}$ in liver and kidney.

4. Experimental Results

The results of release of 2FM-UMP and 2FM-UTP from PA2020, PA2024, PA2029 and sofosbuvir were summarized in Table 7; the result of release of 2FM-UR from PA2029 was summarized in Table 8.

TABLE 7

Exposure amount of monophosphate metabolite 2FM-UMP and triphosphate active molecule 2FM-UTP in liver, heart and plasma within 24 h after intragastric administration of 30 mg/kg PA2020, PA2024, PA2029 and sofosbuvir (h · ng/g, concentration/tissue weight)

| | Liver | | Heart | | Plasma | |
| --- | --- | --- | --- | --- | --- | --- |
| | 2FM-UTP | 2FM-UMP | 2FM-UTP | 2FM-UMP | 2FM-UTP | 2FM-UMP |
| SFB | 2691 | 27128 | N.D. | 417 | N.D. | 5680 |
| PA2020 | 26682 | 102822 | N.D. | N.D. | N.D. | 439 |
| PA2024 | 9591 | 65242 | N.D. | N.D. | N.D. | 105 |
| PA2029 | 11820 | 110339 | N.D. | N.D. | N.D. | 1451 |

N.D. = Not detectable (Representing exposure amount in the corresponding organ or tissue below 5 ng/g or 5 ng/mL)

TABLE 8

Exposure amount of dephosphorylated metabolite 2FM-UR in liver, heart and plasma within 24 h after intragastric administration of 30 mg/kg PA2029 and sofosbuvir (h · ng/g, concentration/tissue weight)

| | Liver | Heart | Plasma |
| --- | --- | --- | --- |
| SFB | 25861 | 6795 | 5968 |
| PA2029 | 37063 | 4676 | 3215 |

4.1 Distribution of Metabolites in Liver (Lesion Tissue)

Figure 2:
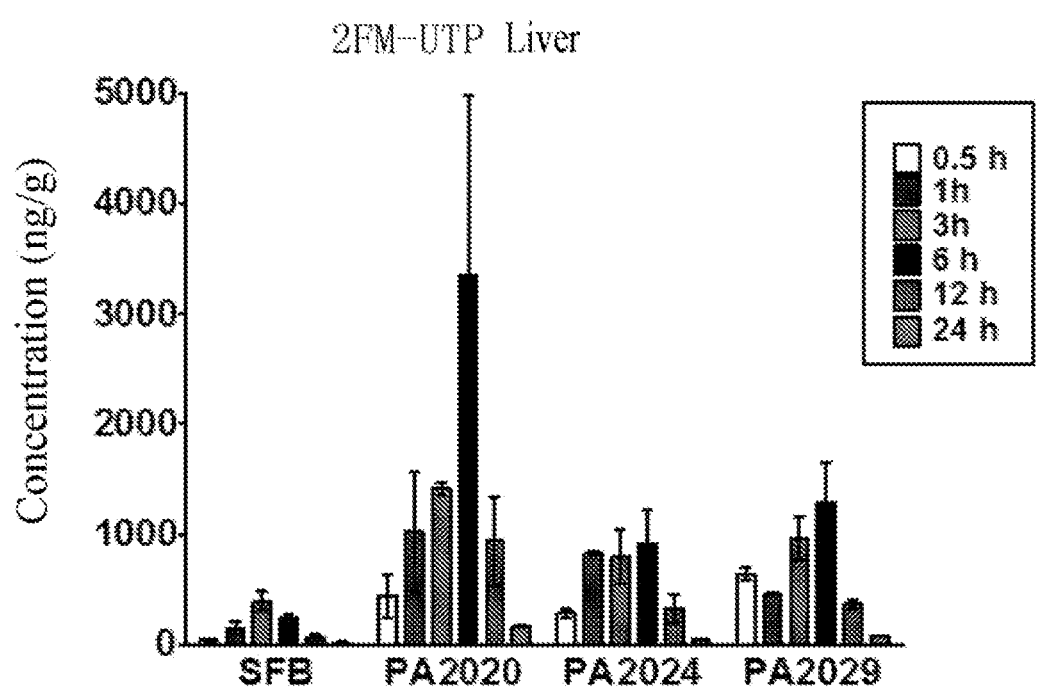
FIG. 2 is a bar chart showing the change of concentration of the active triphosphorus molecule 2FM-UTP in the liver over time after intragastric administration of 30 mg/kg PA2020, PA2024, PA2029 and sofosbuvir to rats (ng/g, concentration/tissue weight).

After 30 mg/Kg of test drug was orally administrated to Sprague Dawley rats, the results of liver tissue distribution showed the active molecule 2FM-UTP released by PA2020, PA2024 and PA2029 were significantly higher than the corresponding time points of sofosbuvir ($p<0.01$, FIG. 2). Using WinNonLin6.2.1 to fit the area under the curve of the drug, the liver exposure of active molecule 2FM-UTP which was the active molecule of the polymerase that inhibited the release of hepatitis C virus from PA2020, PA2024 and PA2029, was 9.9 times that of sofosbuvir (ratio of 26682 h·ng/g to 2691 h·ng/g), 3.6 times (ratio of 9591 h·ng/g to 2691 h·ng/g) and 4.4 times (ratio of 11820 h·ng/g to 2691 h·ng/g) (Table 7). These results indicated that the modification of the liver delivery group significantly increased the distribution of the active molecule 2FM-UTP in the liver compared to sofosbuvir at the same dose.

According to the principle of dose-effect, relationship, it was predicted that the lower doses of series compounds of PA2020, PA2024 and PA2029 could achieve the same clinical efficacy of sofosbuvir.

4.2 Distribution of metabolites in blood and heart (normal tissue)

The lower limit of quantitation (LOD=5 ng/mL, or 5 ng/g) of the established MS/MS assay, PA2020, PA2024, PA2029 and the active molecule 2FM-UTP released from the metabolism of sofosbuvir could not be detected in the blood and heart. The inactive molecule 2FM-UR released from the metabolism of sofosbuvir which was the main metabolite in vivo, was more stable in vivo than the active molecule 2FM-UMP, and thus was associated with various toxic effects which were from sofosbuvir.

Figure 3A:
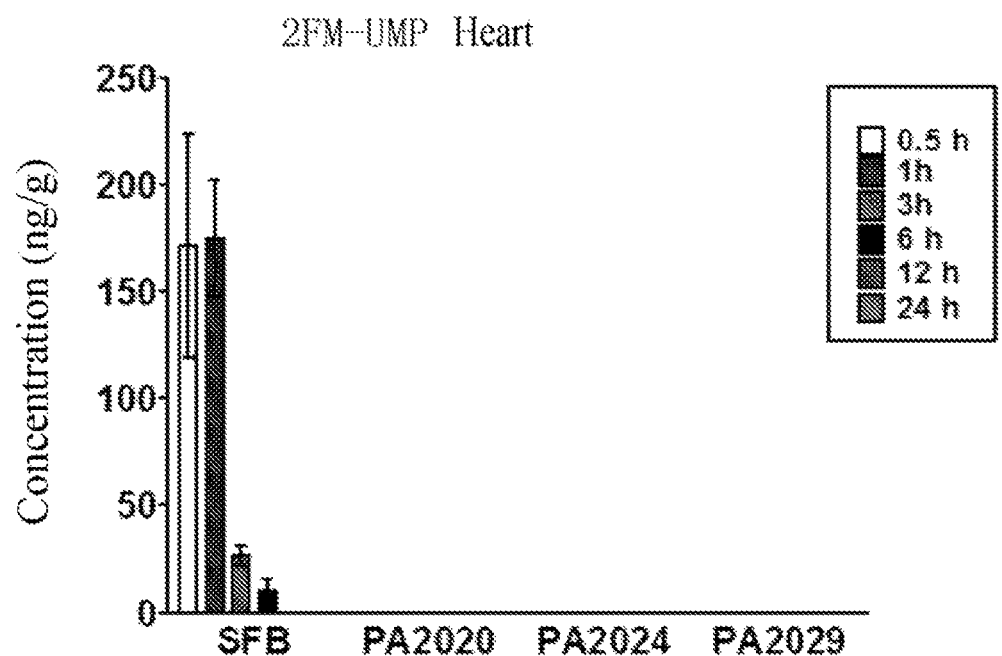
FIGS. 3A-3B respectively show the change of concentration of the monophosphate metabolite 2FM-UMP in heart (A) and plasma (B) over Lime after intragastric administration of 30 mg/kg PA2020, PA2024, PA2029 and sofosbuvir (ng/g, concentration/tissue weight or ng/mL) to rats.
Figure 3B:
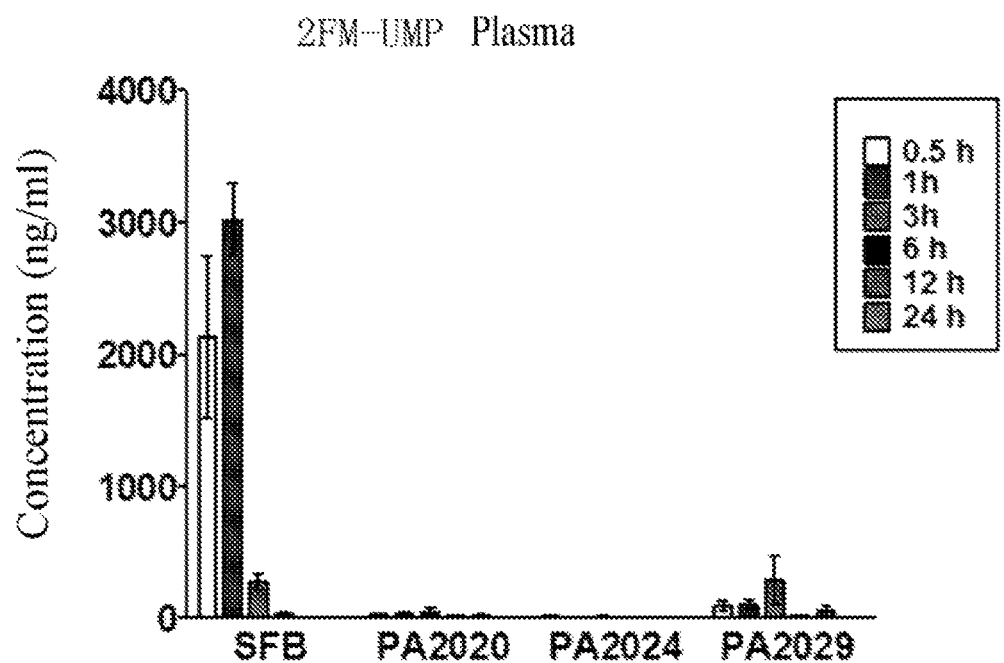
Figure 4A:
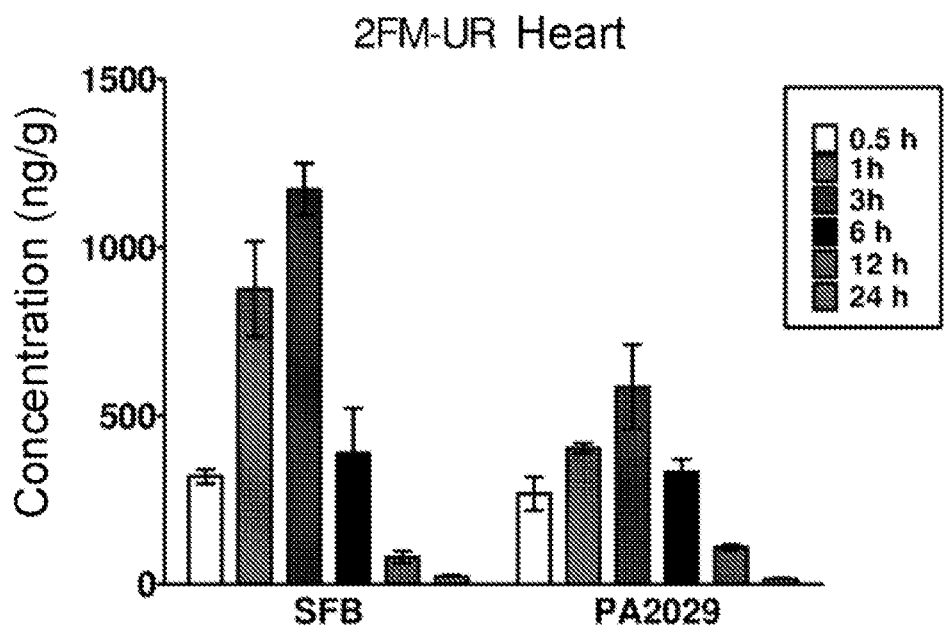
FIGS. 4A-4B respectively show the change of concentration of dephosphorylated metabolite 2FM-UR in heart (A) and plasma (B) over time after intragastric administration of 30 mg/kg PA2029 and sofosbuvir (ng/g, concentration/tissue weight or ng/mL) to rats.
Figure 4B:
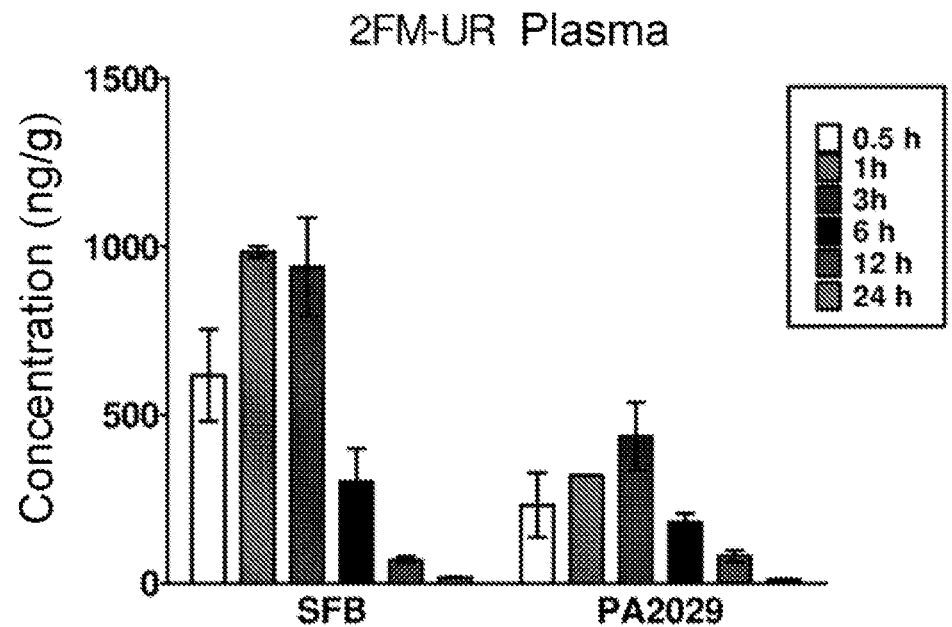

In March 2015, the FDA warned that the treatment of HCV which is a method that combines sofosbuvir with other antiviral drugs and amiodarone could cause severe heart rhythm and may led to death. The high concentration of the monophosphate metabolites 2FM-UMP and 2FM-UR of sofosbuvir in organs or tissues such as the heart may be the main cause of clinical toxicity. PA2020, PA2024 and PA2029 released less 2FM-UMP in the heart than sevofluromide (p<0.01, FIGS. 3A-3B and Table 7); the 2FM-UR released by PA2029 the heart was also less than the equivalent dose of sofosbuvir (p<0.01, FIGS. 4A-4B and Table 8). Therefore, the PA20XX series of compounds of the invention had a significantly lower risk of cardiotoxicity than sofosbuvir at the same dosage.

Patients with severe renal impairment (eGFR<30 mL/min/1.73m2) could affect the elimination of the sofosbuvir metabolites 2FM-UMP and 2FM-UR from the blood, which would aggravate the systemic toxicity caused by metabolites. Therefore, the clinical guidelines for sofosbuvir did not recommend the use of sofosbuvir in such patients, which made the HCV patients with poor renal function lose the opportunity to use sofosbuvir. At the same dose, the 2FM-UMP concentration in plasma of PA2020, PA2024 and PA2029 was only about ⅓, ⅕₄ and ¼ of sofosbuvir (Table 7). The 2FM-UR concentration of PA2029 in plasma was approximately half that of sofosbuvir (Table 8). Therefore, PA2020, PA2024 and PA2029 had the potential to solve the problem that patients with severely impaired renal function failed to receive sofosbuvir in HCV patients.

In summary, the compounds of the formula (II) and formula (III) of the present invention have higher activity and higher tissue specificity for liver delivery, therefore, the amount of treatment required is lower, with higher safety and lower toxic side effects.

All documents mentioned in the present application are hereby incorporated by reference as if each document is individually incorporated by reference. In addition, it should be understood that various modifications and changes may be made to the present invention without departing from the disclosure of the invention. These equivalents also fall within the scope defined by the appended claims.

What is claimed is:
1. A compound of formula (II) or formula (III)

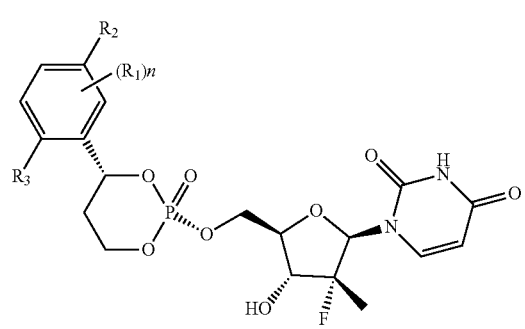
(II)

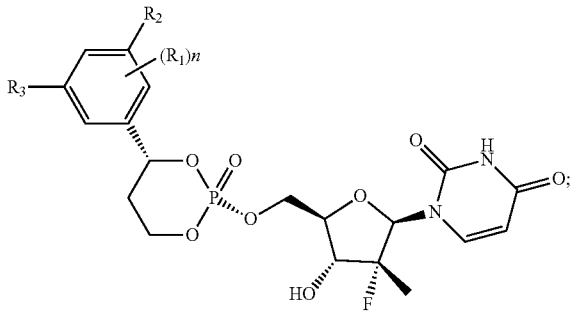
(III)

wherein each $R_1$ is independently selected from halogen, nitro, hydroxyl, amino, cyano group, substituted or unsubstituted $C_1$-$C_6$ alkyl, substituted or unsubstituted $C_3$-$C_8$ cycloalkyl, substituted or unsubstituted $C_1$-$C_6$ alkoxy, substituted or unsubstituted $C_1$-$C_6$ alkylamino, substituted or unsubstituted $C_1$-$C_6$ carboxyl, substituted or unsubstituted $C_1$-$C_6$ ester group, substituted or unsubstituted $C_2$-$C_6$ alkanoyl or substituted or unsubstituted $C_2$-$C_6$ alkylamido; where the substituted groups comprise one or more substituents selected from the group consisting of halogen, $C_1$-$C_3$ alkyl, $C_1$-$C_3$ haloalkyl, nitro, hydroxyl, amino and cyano group;

$R_2$ is Cl and $R_3$ is F; or $R_2$ is F and $R_3$ is Cl;

n is 0, 1, 2 or 3; and each chiral center is R-configuration or S-configuration.

2. The compound of claim 1, wherein the compound of formula (II) is:

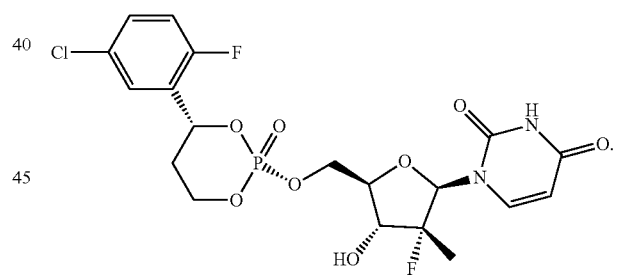

3. The compound of claim 1, wherein the compound of formula (III) is:

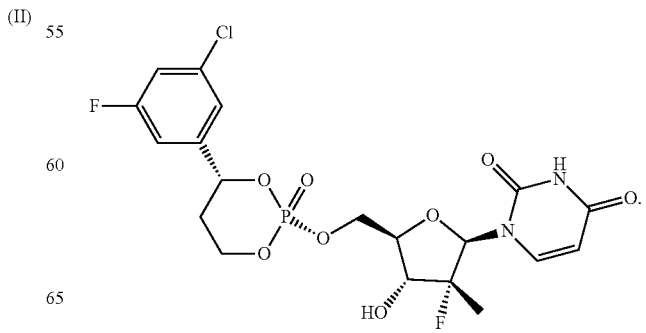

4. The compound of claim 1, wherein the compound is a racemate or an optical isomer thereof.

5. The compound of claim 4, wherein the optical isomer is selected from a tautomer, a cis and trans isomer, a conformational isomer, a mesomer or optical isomers having an enantiomeric or diastereomeric relationship.

6. The compound of claim 2, wherein the compound is an optical isomer thereof, and the optical isomer is selected from a tautomer, a cis and trans isomer, a conformational isomer, a mesomer or optical isomers having an enantiomeric or diastereomeric relationship.

7. The compound of claim 3, wherein the compound is an optical isomer thereof, and the optical isomer is selected from a tautomer, a cis or trans isomer, a conformational isomer, a mesomer or optical isomers having an enantiomeric or diastereomeric relationship.

8. A pharmaceutical composition, comprising the compound of claim 1, or an optical isomer, or a pharmaceutically acceptable salt thereof, and a pharmaceutically-acceptable auxiliary, diluent or carrier.

9. A method for treating hepatitis C virus (HCV) infection in a patient in need thereof, comprising:
  administering to the patient an affective amount of the pharmaceutical composition of claim 8.

* * * * *